US008268316B2

(12) United States Patent
Hong et al.

(10) Patent No.: US 8,268,316 B2

(45) Date of Patent: Sep. 18, 2012

(54) MONOCLONAL ANTIBODY SPECIFIC TO ANTHRAX TOXIN

(75) Inventors: Hyo Jeong Hong, Taejon (KR); Kyung Soo Inn, Taejon (KR); Nam Kyu Lim, Gyeonggi-do (KR); Jung Whan Kim, Taejon (KR); Keun Soo Kim, Gyeonggi-do (KR); Sang Yoon Lee, Taejon (KR); Se Yeon Kim, Chungcheong-buk-do (KR); Hyun Jung Kang, Taejon (KR); Mee Sook Oh, Taejon (KR)

(73) Assignee: Aprogen, Inc, Daejeon (KR)

( * ) Notice: Subject to any disclaimer, the term of this patent is extended or adjusted under 35 U.S.C. 154(b) by 1345 days.

(21) Appl. No.: 11/908,249

(22) PCT Filed: Mar. 10, 2006

(86) PCT No.: PCT/KR2006/000878

§ 371 (c)(1),
(2), (4) Date: Sep. 10, 2007

(87) PCT Pub. No.: WO2006/096039

PCT Pub. Date: Sep. 14, 2006

(65) Prior Publication Data

US 2011/0117104 A1 May 19, 2011

(30) Foreign Application Priority Data

Mar. 11, 2005 (KR) ........................ 10-2005-0020724
Jul. 22, 2005 (KR) ........................ 10-2005-0066875

(51) Int. Cl.
*A61K 39/40* (2006.01)

(52) U.S. Cl. .................... 424/150.1; 435/7.32; 435/340; 435/975; 530/387.3; 530/387.9; 530/388.1; 530/388.4; 536/23.53

(58) Field of Classification Search ........................ None
See application file for complete search history.

(56) References Cited

U.S. PATENT DOCUMENTS 6,180,370 B1 * 1/2001 Queen et al. ................. 435/69.6
2004/0171121 A1 9/2004 Leppla et al.

OTHER PUBLICATIONS

Pannifer et al (Nature, 414:229-233, 2001).*
Campbell (Monoclonal Antibody Technology, Elsevier Science Publishers 1986,pp. 1-32, in particular p. 29, section 1.3.4).*
Lim et al (Infection and Immunity, 73(10):6547-6551, Oct. 2005).*
Jennifer A. Maynard et al., "Protection against anthrax toxin by recombinant antibody fragments correlates with antigen affinity", Nature Publishing Group, Jun. 2002, vol. 20, biotech.nature.com, pp. 597-601.
Zhao, et al, "Neutralizing monoclonal antibody against Anthrax lethal factor inhibits intoxication in a mouse model", Human Antibodies, vol. 12, pp. 129-135; 2003.
Rainey, et al, "Antitoxins: Novel strategies to target agents of bioterrorism", Nature Reviews/Microbiology, vol. 2, pp. 721-726; 2004.
Kobiler, et al, "Efficiency of Protection of Guinea Pigs against Infection with *Bacillus anthracis* Spores by Passive Immunization", Infection and Immunity, vol. 70(2), pp. 544-550; 2002.
Cirino, et al, "Disruption of Anthrax Toxin Binding with the Use of Human Antibodies and Competitive Inhibitors", Infection and Immunity, vol. 67(6), pp. 2957-2963; 1999.
Beedham, et al, "Passive transfer of protection against *Bacillus anthracis* infection in a murine model", vol. 19, pp. 4409-4416; 2001.
Kozel, et al, "mAbs to *Bacillus anthracis* capsular antigen for immunoprotection in anthrax and detection of antigenemia", PNAS, vol. 101(14), pp. 5042-5047; 2004.
Brossier, et al, "Functional Analysis of *Bacillus anthracis* Protective Antigen by Using Neutralizing Monoclonal Antibodies", vol. 72(11), pp. 6313-6317; 2004.
International Search Report and Written Opinion from PCT/KR2006/000878 dated May 29, 2006.

* cited by examiner

*Primary Examiner* — Patricia A Duffy
(74) *Attorney, Agent, or Firm* — Lathrop & Gage LLP; James H. Velema; Brian C. Trinque

(57) ABSTRACT

Disclosed is a monoclonal antibody having very high affinity to anthrax toxin and potent toxin-neutralizing activity. Also disclosed are a composition for neutralizing anthrax toxin comprising the antibody and a kit for detecting anthrax toxin.

30 Claims, 11 Drawing Sheets

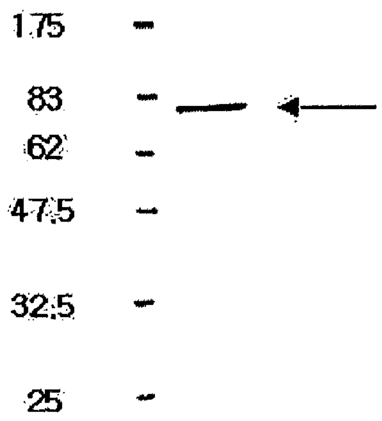
Fig. 5
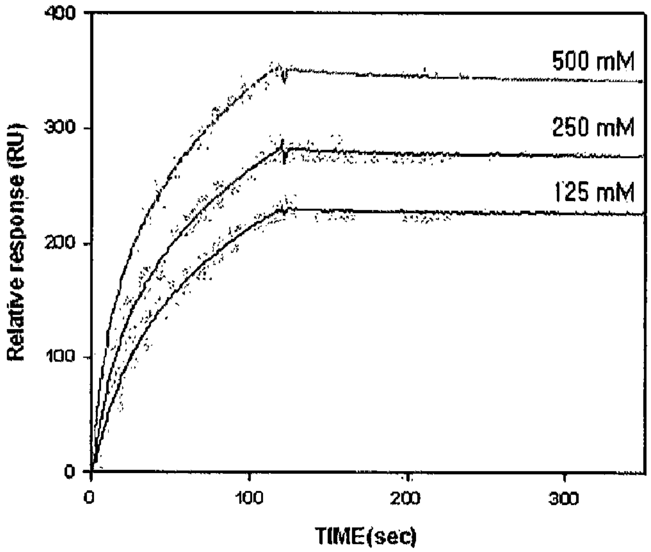
| Antibody | $K_{on}$(1/Ms) | $K_{off}$(1/S) | Kd(M) |
|---|---|---|---|
| 5B13B1 | $4.34 \times 10^4$ | $1.14 \times 10^4$ | 2.2nM |

| | Survival Animal(No.) | Average of time to death |
|---|---|---|
| LeTx only | 0 / 4 | 52 ± 2.45 (min ± SD) |
| 5 min post exposure | 4 / 4 | >24 hrs |
| 15 min post exposure | 2 / 4 | 314.5 ± 105.35 (min ± SD) |
| 30 min post exposure | 0 / 4 | 55.75 ± 2.22 (min ± SD) |

Fig. 13

ANTI-LF (5B13 HEAVY CHAIN)

E V Q L Q Q S G A E L V K P G A S V K L S C T A S G F N I K D S F I H

CDR1

W V K Q R P E Q G L D W I G R I D P A N G N T K Y D P K F Q G K A T L

CDR2

T A D T S S N T A Y L Q L S S L T S E D T A V Y Y C T R L D Y W G Q G

CDR3

ANTI-LF (5B13 KAPPA CHAIN)

E N V L T Q S P A I M S A S L G E R V T M S C R A S P S I N N M Y W Y

CDR1

Q Q K A D A S P R L W I Y Y T S N L A P G V P A R F S G S G S G N S Y

CDR2

S L T I S S M E G E D A A T Y Y C Q Q F T S S P S A L T F G A G T R L

CDR3

E L R

SEQUENCE LISTING

```
<160> NUMBER OF SEQ ID NOS: 42

<210> SEQ ID NO 1
<211> LENGTH: 336
<212> TYPE: DNA
<213> ORGANISM: Mus musculus
<220> FEATURE:
<221> NAME/KEY: CDS
<222> LOCATION: (1)..(336)
<223> OTHER INFORMATION: heavy chain variable region of 5B13B1

<400> SEQUENCE: 1

gag gtg caa ctg cag cag tca ggg gca gag ctt gtg aag cca ggg gcc       48
Glu Val Gln Leu Gln Gln Ser Gly Ala Glu Leu Val Lys Pro Gly Ala
  1               5                  10                  15

tca gtc aag ttg tcc tgc aca gct tct ggc ttc aac att aaa gac tcc       96
Ser Val Lys Leu Ser Cys Thr Ala Ser Gly Phe Asn Ile Lys Asp Ser
             20                  25                  30

ttt ata cac tgg gtg aaa cag agg cct gaa cag ggc ctg gac tgg att      144
Phe Ile His Trp Val Lys Gln Arg Pro Glu Gln Gly Leu Asp Trp Ile
         35                  40                  45

gga agg att gat cct gcg aat ggt aat act aaa tat gac ccg aag ttc      192
Gly Arg Ile Asp Pro Ala Asn Gly Asn Thr Lys Tyr Asp Pro Lys Phe
     50                  55                  60

cag ggc aag gcc act tta aca gca gac aca tcc tcc aac aca gcc tac      240
Gln Gly Lys Ala Thr Leu Thr Ala Asp Thr Ser Ser Asn Thr Ala Tyr
 65                  70                  75                  80

ctg cag ctc agc agc ctg aca tct gag gac act gcc gtc tat tac tgt      288
Leu Gln Leu Ser Ser Leu Thr Ser Glu Asp Thr Ala Val Tyr Tyr Cys
                 85                  90                  95

act aga ctt gac tat tgg ggc caa ggc acc gct ctc aca gtc tcc tca      336
Thr Arg Leu Asp Tyr Trp Gly Gln Gly Thr Ala Leu Thr Val Ser Ser
            100                 105                 110


<210> SEQ ID NO 2
<211> LENGTH: 112
<212> TYPE: PRT
<213> ORGANISM: Mus musculus

<400> SEQUENCE: 2

Glu Val Gln Leu Gln Gln Ser Gly Ala Glu Leu Val Lys Pro Gly Ala
  1               5                  10                  15

Ser Val Lys Leu Ser Cys Thr Ala Ser Gly Phe Asn Ile Lys Asp Ser
             20                  25                  30

Phe Ile His Trp Val Lys Gln Arg Pro Glu Gln Gly Leu Asp Trp Ile
         35                  40                  45
```

-continued

```
Gly Arg Ile Asp Pro Ala Asn Gly Asn Thr Lys Tyr Asp Pro Lys Phe
     50                  55                  60

Gln Gly Lys Ala Thr Leu Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Arg Leu Asp Tyr Trp Gly Gln Gly Thr Ala Leu Thr Val Ser Ser
            100                 105                 110


<210> SEQ ID NO 3
<211> LENGTH: 5
<212> TYPE: PRT
<213> ORGANISM: Mus musculus

<400> SEQUENCE: 3

Asp Ser Phe Ile His
  1               5


<210> SEQ ID NO 4
<211> LENGTH: 17
<212> TYPE: PRT
<213> ORGANISM: Mus musculus

<400> SEQUENCE: 4

Arg Ile Asp Pro Ala Asn Gly Asn Thr Lys Tyr Asp Pro Lys Phe Gln
  1               5                  10                  15

Gly


<210> SEQ ID NO 5
<211> LENGTH: 3
<212> TYPE: PRT
<213> ORGANISM: Mus musculus

<400> SEQUENCE: 5

Leu Asp Tyr
  1


<210> SEQ ID NO 6
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION: light chain variable region of 5B13B1

<400> SEQUENCE: 6

gaa aat gtg ctg aca caa tct cca gca atc atg tct gca tct cta ggg       48
Glu Asn Val Leu Thr Gln Ser Pro Ala Ile Met Ser Ala Ser Leu Gly
  1               5                  10                  15

gag aag gtc acc atg agc tgc agg gcc agc cca agt ata aat aac atg       96
Glu Lys Val Thr Met Ser Cys Arg Ala Ser Pro Ser Ile Asn Asn Met
             20                  25                  30

tac tgg tac cag cag aag gca gac gcc tcc ccc aaa cta tgg att tat      144
Tyr Trp Tyr Gln Gln Lys Ala Asp Ala Ser Pro Lys Leu Trp Ile Tyr
         35                  40                  45

tac aca tcc aac ctg gct cct gga gtc cca gct cgc ttc agt ggc agt      192
Tyr Thr Ser Asn Leu Ala Pro Gly Val Pro Ala Arg Phe Ser Gly Ser
     50                  55                  60

ggg tct ggg aac tct tat tct ctc aca atc agc agc atg gag ggt gaa      240
Gly Ser Gly Asn Ser Tyr Ser Leu Thr Ile Ser Ser Met Glu Gly Glu
 65                  70                  75                  80
```

-continued

```
gat gct gcc act tat tac tgc cag cag ttt act agt tcc cca tcc gcg      288
Asp Ala Ala Thr Tyr Tyr Cys Gln Gln Phe Thr Ser Ser Pro Ser Ala
                 85                  90                  95

ctc acg ttc ggt gct ggg acc aag ctg gag ctg aaa                      324
Leu Thr Phe Gly Ala Gly Thr Lys Leu Glu Leu Lys
            100                 105


<210> SEQ ID NO 7
<211> LENGTH: 108
<212> TYPE: PRT
<213> ORGANISM: Mus musculus

<400> SEQUENCE: 7

Glu Asn Val Leu Thr Gln Ser Pro Ala Ile Met Ser Ala Ser Leu Gly
  1               5                  10                  15

Glu Lys Val Thr Met Ser Cys Arg Ala Ser Pro Ser Ile Asn Asn Met
             20                  25                  30

Tyr Trp Tyr Gln Gln Lys Ala Asp Ala Ser Pro Lys Leu Trp Ile Tyr
         35                  40                  45

Tyr Thr Ser Asn Leu Ala Pro Gly Val Pro Ala Arg Phe Ser Gly Ser
     50                  55                  60

Gly Ser Gly Asn Ser Tyr Ser Leu Thr Ile Ser Ser Met Glu Gly Glu
 65                  70                  75                  80

Asp Ala Ala Thr Tyr Tyr Cys Gln Gln Phe Thr Ser Ser Pro Ser Ala
                 85                  90                  95

Leu Thr Phe Gly Ala Gly Thr Lys Leu Glu Leu Lys
            100                 105


<210> SEQ ID NO 8
<211> LENGTH: 10
<212> TYPE: PRT
<213> ORGANISM: Mus musculus

<400> SEQUENCE: 8

Arg Ala Ser Pro Ser Ile Asn Asn Met Tyr
  1               5                  10


<210> SEQ ID NO 9
<211> LENGTH: 7
<212> TYPE: PRT
<213> ORGANISM: Mus musculus

<400> SEQUENCE: 9

Tyr Thr Ser Asn Leu Ala Pro
  1               5


<210> SEQ ID NO 10
<211> LENGTH: 11
<212> TYPE: PRT
<213> ORGANISM: Mus musculus

<400> SEQUENCE: 10

Gln Gln Phe Thr Ser Ser Pro Ser Ala Leu Thr
  1               5                  10


<210> SEQ ID NO 11
<211> LENGTH: 31
<212> TYPE: DNA
<213> ORGANISM: Artificial Sequence
<220> FEATURE:
<223> OTHER INFORMATION: primer for amplification of lethal factor
```

-continued

<400> SEQUENCE: 11
cgtggatcca tggcgggcgg tcatggtgat g 31

<210> SEQ ID NO 12
<211> LENGTH: 28
<212> TYPE: DNA
<213> ORGANISM: Artificial Sequence
<220> FEATURE:
<223> OTHER INFORMATION: primer for amplification of lethal factor

<400> SEQUENCE: 12
gattctagat tatgagttaa taatgaac 28

<210> SEQ ID NO 13
<211> LENGTH: 32
<212> TYPE: DNA
<213> ORGANISM: Artificial Sequence
<220> FEATURE:
<223> OTHER INFORMATION: primer for amplification of heavy chain variable region of 5B13B1

<400> SEQUENCE: 13
atatgtcgac aggtsmaact gcagsagtcw gg 32

<210> SEQ ID NO 14
<211> LENGTH: 31
<212> TYPE: DNA
<213> ORGANISM: Artificial Sequence
<220> FEATURE:
<223> OTHER INFORMATION: primer for amplification of heavy chain variable region of 5B13B1

<400> SEQUENCE: 14
cggtcgacag ggatccagag ttccaggtca c 31

<210> SEQ ID NO 15
<211> LENGTH: 45
<212> TYPE: DNA
<213> ORGANISM: Artificial Sequence
<220> FEATURE:
<223> OTHER INFORMATION: primer for amplification of light chain variable region of 5B13B1

<400> SEQUENCE: 15
cagcatgtgg cccaggcggc cgayattgtg mtsacmcarw ctmca 45

<210> SEQ ID NO 16
<211> LENGTH: 31
<212> TYPE: DNA
<213> ORGANISM: Artificial Sequence
<220> FEATURE:
<223> OTHER INFORMATION: primer for amplification of light chain variable region of 5B13B1

<400> SEQUENCE: 16
gcagtcgact gaggcacctc cagatgttaa c 31

<210> SEQ ID NO 17
<211> LENGTH: 24
<212> TYPE: DNA
<213> ORGANISM: Artificial Sequence
<220> FEATURE:
<223> OTHER INFORMATION: primer for amplification of heavy chain variable region of 5B13B1

<400> SEQUENCE: 17
cagagtgagg tgcaactgca gcag 24

<210> SEQ ID NO 18
<211> LENGTH: 39
<212> TYPE: DNA
<213> ORGANISM: Artificial Sequence
<220> FEATURE:
<223> OTHER INFORMATION: primer for amplification of heavy chain
variable region of 5B13B1

<400> SEQUENCE: 18
gatgggccct tcgtgctggc tgaggagact gtgagagcg 39

<210> SEQ ID NO 19
<211> LENGTH: 30
<212> TYPE: DNA
<213> ORGANISM: Artificial Sequence
<220> FEATURE:
<223> OTHER INFORMATION: primer for amplification of light chain
variable region of 5B13B1

<400> SEQUENCE: 19
ctgtggggaa aatgtgctga cacaatctcc 30

<210> SEQ ID NO 20
<211> LENGTH: 32
<212> TYPE: DNA
<213> ORGANISM: Artificial Sequence
<220> FEATURE:
<223> OTHER INFORMATION: primer for amplification of light chain
variable region of 5B13B1

<400> SEQUENCE: 20
ccaccgtacg tttcagctcc agcttggtcc ca 32

<210> SEQ ID NO 21
<211> LENGTH: 26
<212> TYPE: DNA
<213> ORGANISM: Artificial Sequence
<220> FEATURE:
<223> OTHER INFORMATION: primer for amplification of leader sequence
of heavy chain

<400> SEQUENCE: 21
gagaattcac attcacgatg tacttg 26

<210> SEQ ID NO 22
<211> LENGTH: 29
<212> TYPE: DNA
<213> ORGANISM: Artificial Sequence
<220> FEATURE:
<223> OTHER INFORMATION: primer for amplification of leader sequence
of heavy chain

<400> SEQUENCE: 22
gttgcacctc actctggaca ccatttaag 29

<210> SEQ ID NO 23
<211> LENGTH: 30
<212> TYPE: DNA
<213> ORGANISM: Artificial Sequence
<220> FEATURE:
<223> OTHER INFORMATION: primer for amplification of leader sequence
of light chain

<400> SEQUENCE: 23
gctgcaaagc ttggaagcaa gatggattca 30

-continued

```
<210> SEQ ID NO 24
<211> LENGTH: 27
<212> TYPE: DNA
<213> ORGANISM: Artificial Sequence
<220> FEATURE:
<223> OTHER INFORMATION: primer for amplification of leader sequence
      of light chain

<400> SEQUENCE: 24

agcacatttt ccccacaggt accagat                                          27


<210> SEQ ID NO 25
<211> LENGTH: 57
<212> TYPE: DNA
<213> ORGANISM: Homo sapiens

<400> SEQUENCE: 25

atgtacttgg gactgaacta tgtattcata gtttttctct taaatggtgt ccagagt         57


<210> SEQ ID NO 26
<211> LENGTH: 60
<212> TYPE: DNA
<213> ORGANISM: Homo sapiens

<400> SEQUENCE: 26

atggattcac aggcccaggt tcttatgtta ctgctgctat gggtatctgg tacctgtggg      60


<210> SEQ ID NO 27
<211> LENGTH: 31
<212> TYPE: DNA
<213> ORGANISM: Artificial Sequence
<220> FEATURE:
<223> OTHER INFORMATION: primer 1-3F

<400> SEQUENCE: 27

aatggatcca tggcgggcgg tcatggtgat g                                     31


<210> SEQ ID NO 28
<211> LENGTH: 31
<212> TYPE: DNA
<213> ORGANISM: Artificial Sequence
<220> FEATURE:
<223> OTHER INFORMATION: primer 1R

<400> SEQUENCE: 28

gattctagag gatagattta tttcttgttc g                                     31


<210> SEQ ID NO 29
<211> LENGTH: 28
<212> TYPE: DNA
<213> ORGANISM: Artificial Sequence
<220> FEATURE:
<223> OTHER INFORMATION: primer 2R

<400> SEQUENCE: 29

atttctagat taaatatcaa gtttcagc                                         28


<210> SEQ ID NO 30
<211> LENGTH: 31
<212> TYPE: DNA
<213> ORGANISM: Artificial Sequence
<220> FEATURE:
<223> OTHER INFORMATION: primer 3R

<400> SEQUENCE: 30

atttctagat tacactactt tcgcatcaat c                                     31
```

-continued

<210> SEQ ID NO 31
<211> LENGTH: 32
<212> TYPE: DNA
<213> ORGANISM: Artificial Sequence
<220> FEATURE:
<223> OTHER INFORMATION: primer 4R

<400> SEQUENCE: 31
atttctagat tatgagttaa taatgaactt aa 32

<210> SEQ ID NO 32
<211> LENGTH: 30
<212> TYPE: DNA
<213> ORGANISM: Artificial Sequence
<220> FEATURE:
<223> OTHER INFORMATION: primer 4F

<400> SEQUENCE: 32
attggatcca tgaagaaaga tgacataatt 30

<210> SEQ ID NO 33
<211> LENGTH: 34
<212> TYPE: DNA
<213> ORGANISM: Artificial Sequence
<220> FEATURE:
<223> OTHER INFORMATION: primer 5F

<400> SEQUENCE: 33
ggaagaactt aaagatcaaa agaaagatga cata 34

<210> SEQ ID NO 34
<211> LENGTH: 34
<212> TYPE: DNA
<213> ORGANISM: Artificial Sequence
<220> FEATURE:
<223> OTHER INFORMATION: primer 5R

<400> SEQUENCE: 34
tatgtcatct ttcttttgat ctttaagttc ttcc 34

<210> SEQ ID NO 35
<211> LENGTH: 35
<212> TYPE: DNA
<213> ORGANISM: Artificial Sequence
<220> FEATURE:
<223> OTHER INFORMATION: primer 6F

<400> SEQUENCE: 35
gattcctatt gagccacaac catatgatat taatc 35

<210> SEQ ID NO 36
<211> LENGTH: 35
<212> TYPE: DNA
<213> ORGANISM: Artificial Sequence
<220> FEATURE:
<223> OTHER INFORMATION: primer 6R

<400> SEQUENCE: 36
gattaatatc atatggttgt ggctcaatag gaatc 35

<210> SEQ ID NO 37
<211> LENGTH: 18
<212> TYPE: PRT
<213> ORGANISM: Artificial Sequence
<220> FEATURE:
<223> OTHER INFORMATION: peptide R2

-continued

<400> SEQUENCE: 37

His Ser Leu Ser Gln Glu Glu Lys Glu Leu Leu Lys Arg Ile Gln Ile
1 5 10 15

Asp Cys

<210> SEQ ID NO 38
<211> LENGTH: 20
<212> TYPE: PRT
<213> ORGANISM: Artificial Sequence
<220> FEATURE:
<223> OTHER INFORMATION: peptide R3

<400> SEQUENCE: 38

Ser Asp Phe Leu Ser Thr Glu Glu Lys Glu Phe Leu Lys Lys Leu Gln
1 5 10 15

Ile Asp Ile Cys
20

<210> SEQ ID NO 39
<211> LENGTH: 19
<212> TYPE: PRT
<213> ORGANISM: Artificial Sequence
<220> FEATURE:
<223> OTHER INFORMATION: peptide R4

<400> SEQUENCE: 39

Asp Ser Leu Ser Glu Glu Glu Lys Glu Leu Leu Asn Arg Ile Gln Val
1 5 10 15

Asp Ser Cys

<210> SEQ ID NO 40
<211> LENGTH: 19
<212> TYPE: PRT
<213> ORGANISM: Artificial Sequence
<220> FEATURE:
<223> OTHER INFORMATION: peptide R5

<400> SEQUENCE: 40

Asn Pro Leu Ser Glu Lys Glu Lys Glu Phe Leu Lys Lys Leu Lys Leu
1 5 10 15

Asp Ile Cys

<210> SEQ ID NO 41
<211> LENGTH: 20
<212> TYPE: PRT
<213> ORGANISM: Artificial Sequence
<220> FEATURE:
<223> OTHER INFORMATION: peptide derived from F protein

<400> SEQUENCE: 41

Asn Lys Ile Lys Ser Ala Leu Leu Ser Thr Asn Lys Ala Val Val Ser
1 5 10 15

Leu Ser Asn Cys
20

<210> SEQ ID NO 42
<211> LENGTH: 81
<212> TYPE: PRT
<213> ORGANISM: Bacillus anthracis
<220> FEATURE:
<221> NAME/KEY: PEPTIDE
<222> LOCATION: (1)..(81)
<223> OTHER INFORMATION: domain 3 of lethal factor -continued

```
<400> SEQUENCE: 42

Lys Lys Asp Asp Ile Ile His Ser Leu Ser Gln Glu Glu Lys Glu Leu
  1               5                  10                  15

Leu Lys Arg Ile Gln Ile Asp Ser Ser Asp Phe Leu Ser Thr Glu Glu
             20                  25                  30

Lys Glu Phe Leu Lys Lys Leu Gln Ile Asp Ile Arg Asp Ser Leu Ser
         35                  40                  45

Glu Glu Glu Lys Glu Leu Leu Asn Arg Ile Gln Val Asp Ser Ser Asn
     50                  55                  60

Pro Leu Ser Glu Lys Glu Lys Glu Phe Leu Lys Lys Leu Lys Leu Asp
 65                  70                  75                  80

Ile
```

MONOCLONAL ANTIBODY SPECIFIC TO ANTHRAX TOXIN

TECHNICAL FIELD

The present invention relates to a monoclonal antibody specifically binding to anthrax toxin. The present invention is also concerned with a composition for neutralizing anthrax toxin and a kit for detecting anthrax toxin, comprising the antibody.

BACKGROUND ART

*Bacillus anthracis* is Gram-positive, 4-8 μm in length and 1-1.5 μm in width, making it the largest among pathogens, is square-ended, and sometimes forms long chains. *B. anthracis* is non-motile without flagella, and forms spores in unfavorable environments The spores can survive for 24 hours in air and even for 100 years in the soil, and have properties of high resistance to heat, sunlight, disinfecting agents, and the like.

Anthrax is a disease caused by a spore-forming bacterium belonging to the genus *Bacillus, Bacillus anthracis*. Since anthrax is actually rare in humans, studies involving anthrax have been not actively performed. Anthrax most commonly occurs in domestic animals (cattle, sheep, goats, camels, antelopes, and other herbivores), and often occurs in livestock workers who are exposed to infected livestock, or in people when they ingest products made from infected livestock. However, due to its high potential use for purposes of biological terrorism, *B. anthracis* has recently been classified by the American CDC (Centers for disease control and prevention) as a pathogenic microorganism of Category A, which has high potential for use in terrorism.

Anthrax infection may occur mainly in three forms: cutaneous (skin), inhalation (pulmonary), and intestinal. Among them, inhalation infection is most lethal. Initial symptoms of inhalation anthrax may resemble a common cold and include fever, difficulty in breathing, coughing, headaches, vomiting, chilling, abdominal pain, and chest discomfort After several days, the symptoms may progress to severe breathing problems and shock. Inhalation anthrax is usually fatal. About 20% of all cutaneous infection cases are fatal, and intestinal infection results in a 25-60% death rate. Inhalation infection is more frequently fatal.

In the case of inhalation anthrax, *B. anthracis* is drawn in its dormant spore state into the lungs through the respiratory tract, and is ingested by macrophages in the alveoli. The spores germinate within the macrophages, and are carried to lymph nodes, where they multiply. The bacterial cells then get into the bloodstream, and begin reproducing continuously and producing toxins, causing lethal symptoms (Maynard et al., Nature Biotechnology 2002 20:597-601).

*B. anthracis* produces anthrax toxin through a pXO1 plasmid. Anthrax toxin is composed of three distinct proteins: protective antigen (PA, 83 kDa), lethal factor (LF, 90 kDa), and edema factor (EF, 89 kDa). The protective antigen, consisting of four folding domains, binds to the anthrax toxin receptor (ATR) on the cell surface through its domain 4. PA is then cleaved at the site of domain 1 by furin-like protease on the cell surface to produce PA63, releasing an N-terminal 20-kDa fragment The activated form of PA, PA63, oligomerizes into a heptamer, $[PA63]_7$, to generate regions capable of binding to LF or EF. The PA63 heptamer combines with either LF or EF to form either lethal toxin (LeTx) or edema toxin (EdTx).

The PA63 heptamer-LF/EF complex is endocytosed into the cytoplasm, and fused with lysosome. The PA63 heptamer undergoes conformational changes at low pH, resulting in the release of LF and EF into the cytoplasm. In the cytoplasm, LF acts as a zinc-dependent metalloprotease which cleaves mitogen-activated protein kinase kinases. This cleavage disrupts the intracellular signal transduction pathway, resulting in the lysis of macrophages. EF is a calcium/calmodulin-dependent adenylate cyclase, which causes increased levels of intracellular cAMP levels, leading to swelling and local inflammation, which are generally not lethal.

At present, several antibiotics, such as penicillin, doxycycline, and fluroquinolones, are used for the treatment of anthrax infections. However, antibiotic treatment cannot be applied to antibiotic-resistant anthrax strains. In particular, this antibiotic treatment is not suitable for use in biochemical terrorism or biochemical warfare, which uses antibiotic-resistant strains. Also, since antibiotics cannot inhibit the action of anthrax toxin, anthrax is highly fatal if antibiotics are not administered at early stages of infection. Unfortunately, anthrax is difficult to diagnose and treat at early stages because it initially presents with cold-like symptoms.

Vaccines, whose major component is PA, have been developed and are currently used for preventing anthrax in the USA and Great Britain. However, since the vaccines have not been proven completely safe, their application is allowed only to army personnel and some persons who are highly liable to be exposed to *B. anthracis*. In addition, since a period of at least several months is required to acquire sufficient immunity, vaccines are actually impossible to apply in emergency situations such as in the event of biochemical terrorism. Thus, there is an urgent need for the development of therapeutic and preventive approaches, other than antibiotics, which can be applied to such situations.

Passive immunization using antibodies is a very effective strategy for toxin neutralization. In fact, the development of antibodies capable of neutralizing botulinum toxin and ricin in addition to anthrax toxin is in progress (Rainey et al., 2004 Nature reviews of Microbiology 2: 721-726). Several research groups revealed through studies using cells and small animals, such as guinea pigs, rats, mice, and hamsters, that antisera are very effective in neutralizing anthrax toxin.

Many attempts have recently been made to neutralize anthrax toxin using monoclonal antibodies against protective antigen (PA) and lethal factor (LF), and such attempts were reported to be successful in practice (Kobiler et al., 2002 Infection and Immunity 70:544-550; Cirino et al., 1999 Infection and Immunity 67:2957-2963; Beedham et al., 2001 Vaccine 19:4409-4416). Antibody-based neutralization of anthrax toxin may occur through a mechanism, such as binding inhibition between PA and its cellular receptor, inhibition of cleavage of PA, binding inhibition between PA and LF, and inhibition of the action of LF. For example, a monoclonal antibody, LF8, capable of neutralizing anthrax toxin, inhibits lethal toxin formation by binding to the PA binding domain of LF or near this domain (Zhao et al., 2003 Human Antibodies 12:129-135).

Taking the importance of antibodies into consideration, there is a need for the development of monoclonal antibodies having high specificity and affinity to antigens and thus being capable of effectively neutralizing anthrax toxin, leading to the effective prevention and treatment of anthrax.

In this regard, the present inventors selected hybridoma cells that secrete monoclonal antibodies capable of neutralizing anthrax toxin by binding to the lethal factor, and found through in vitro cell and in vivo animal studies using Fisher rats that the antibodies produced by the hybridomas have strong toxin-neutralizing activity. The present inventors also found that the antibodies have high affinity to their antigen and exhibit a preventive effect before exposure to anthrax toxin as well as a therapeutic effect after exposure to anthrax toxin. The present inventors further found that the antibodies have a neutralization mechanism different from that of a conventional antibody, LF8, and have higher cytotoxicity-neutralizing activity than the LF8 antibody. The present inventors also identified amino acid sequences of heavy chain and light chain variable regions of the antibodies and CDR regions of the variable regions, thereby leading to the present invention.

DISCLOSURE OF THE INVENTION

It is therefore an object of the present invention to provide a monoclonal antibody specifically binding to anthrax toxin, comprising a heavy chain variable region having an amino acid sequence represented by SEQ ID No. 2 and a light chain variable region having an amino acid sequence represented by SEQ ID No. 7.

It is another object of the present invention to provide a humanized antibody specifically binding to anthrax toxin, comprising a humanized heavy chain variable region that includes complementarity determining regions (CDRs) derived from the heavy chain variable region of the aforementioned antibody and having amino acid sequences represented by SEQ ID Nos. 3, 4 and 5 and a framework region (FR) derived from a heavy chain of a human antibody; and a humanized light chain variable region that includes CDRs derived from the light chain variable region of the aforementioned antibody and having amino acid sequences represented by SEQ ID Nos. 8, 9 and 10 and an FR derived from a light chain of a human antibody.

It is a further object of the present invention to provide a monoclonal antibody specifically binding to anthrax toxin, which is produced by a hybridoma having accession number KCTC 10756BP.

It is yet another object of the present invention to provide a hybridoma having accession number KCTC 10756BP.

It is still another object of the present invention to provide a monoclonal antibody specifically recognizing the domain III of *Bacillus anthracis* lethal factor.

It is still another object of the present invention to provide a nucleotide sequence encoding a heavy chain variable region having an amino acid sequence represented by SEQ ID No. 2.

It is still another object of the present invention to provide a nucleotide sequence encoding a light chain variable region having an amino acid sequence represented by SEQ ID No. 7.

It is still another object of the present invention to provide a composition for neutralizing anthrax toxin, comprising the antibody.

It is still another object of the present invention to provide a method of preventing or treating anthrax by administering the antibody.

It is still another object of the present invention to provide a kit for detecting anthrax toxin, comprising the antibody.

BRIEF DESCRIPTION OF THE DRAWINGS

The above and other objects, features and other advantages of the present invention will be more clearly understood from the following detailed description taken in conjunction with the accompanying drawings, in which:

FIG. 5 shows the results of the evaluation of antigen binding activity of selected antibodies using surface plasmon resonance;

FIG. 13 shows the amino add sequences of CDR1, CDR2 and CDR3 of the heavy chain of the 5B13B1 antibody;

FIG. 14 shows the amino add sequences of CDR1, CDR2 and CDR3 of the light chain of the 5B13B1 antibody;

BEST MODE FOR CARRYING OUT THE INVENTION

Figure 1:
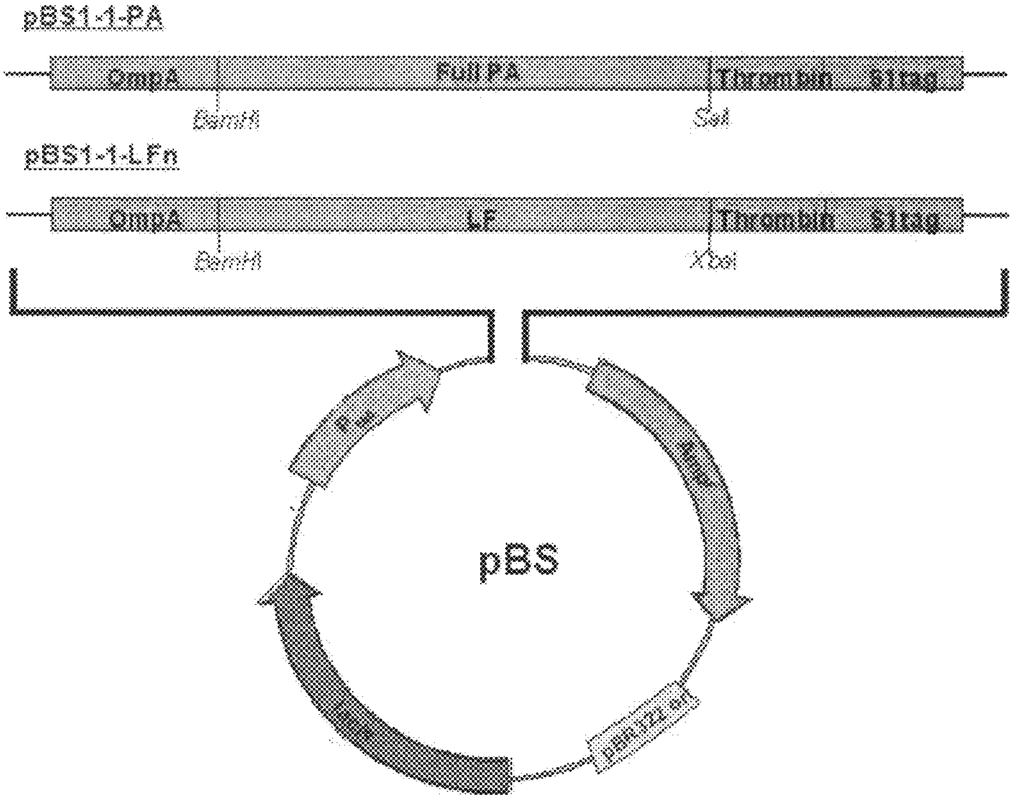
FIG. 1 schematically shows expression vectors constructed for expressing anthrax toxin protective antigen and lethal factor in *E. coli*, wherein restriction enzymes used for insertion into a pBS plasmid are indicated.

The present invention relates to a monoclonal antibody specifically binding to anthrax toxin.

In a detailed aspect, the present invention relates to a monoclonal antibody specifically binding to anthrax toxin, comprising a heavy chain variable region having the amino acid sequence represented by SEQ ID No. 2 and a light chain variable region having the amino acid sequence represented by SEQ ID No. 7.

The present inventors produced monoclonal antibodies specific to anthrax toxin using a known hybridoma method (Kohler and Milstein (1976) European Journal of Immunology 6:511-519). In detail, anthrax lethal factor was expressed in *E. coli* and purified, and mice were immunized by injection of the purified antigen. Splenocytes were extracted from the immunized mice and fused with myeloma F0 cells using polyethylene glycol. The fused cells were cultured and assessed for neutralizing activity. Antibody-producing cells having anthrax toxin-neutralizing activity were subjected to limited dilution in order to select hybridomas producing uniform antibodies, and finally, two monoclonal antibodies, 5B13B1 and 3C16C3, were selected. The monoclonal antibodies produced by the hybridomas were assessed for LF-binding activity using ELISA and LeTx-neutralizing activity through the evaluation of cell survival rates (%). The 5B13B1 monoclonal antibody exhibited an LF-binding activity of 1.517 and an LeTx-neutralizing activity of 99.7%, and the 3C16C3 monoclonal antibody displayed an LF-binding activity of 1.72 and an LeTx-neutralizing activity of 104.3% (Table 1). An amino acid sequence analysis of variable regions resulted in the finding that the heavy chain variable region of the 5B13B1 monoclonal antibody has the amino acid sequence represented by SEQ ID No. 2 and the light chain variable region of the antibody has the amino acid sequence represented by SEQ ID No. 7.

The term “antibody”, as used herein, refers to a molecule specifically binding to an antigen. With respect to the objects of the present invention, the term “antibody” indicates a molecule specifically binding to anthrax toxin, and is a monoclonal antibody specifically binding to anthrax toxin lethal factor (LF) as well as lethal toxin (LeTx).

The antibodies of the present invention are neutralizing antibodies. The term “neutralizing antibody” means an antibody that induces a neutralizing immune response by removing or significantly reducing the biological activity or effector functions of a bound target antigen. The 5B13B1 and 3C16C3 antibodies of the present invention are characterized in that they are neutralizing antibodies capable of preventing or treating anthrax by removing or significantly reducing the functions of lethal factor or lethal toxin (for example, participating in the formation of giant cells and the invasion and attachment of viruses).

The antibodies of the present invention have potent toxin-neutralizing activity and high affinity to their antigen. When murine macrophage J774A.1 cells were exposed to 400 μg/ml of protective antigen and 200 μg/ml of lethal factor, the deduced $IC_{50}$ values of the 5B13B1 and 3C16C3 antibodies were 0.212 μg/ml and 0.604 μg/ml, respectively, indicating that the 5B13B1 antibody has potent neutralizing activity. Also, the 5B13B1 antibody, which exhibits a $K_d$ of 2.2 nM for its antigen, lethal factor, has a very high affinity to the antigen. The term “$K_d$”, as used herein, refers to the dissociation constant of a specific antibody-antigen interaction, and is used to measure the affinity of an antibody to an antigen.

The antibodies of the present invention are novel neutralizing antibodies, which have higher affinity than conventional LF8 antibody and are effective in the prevention and treatment of anthrax through a neutralization mechanism different from that of the conventional LF8 antibody. The neutralization mechanism of the 5B13B1 antibody of the present invention was compared with that of the conventional LF8 antibody. As a result, unlike the LF8 antibody, which inhibits the binding of protective antigen (PA) and lethal factor (LF) by binding to the PA-binding domain of LF or near this domain, the 5B13B1 antibody binds to region other than the PA-binding domain of LF, and is thus able to bind to lethal toxin as well as LF. Also, when the toxin-neutralizing activity of the 5B13B1 and LF8 antibodies was assessed in cells treated with 5 μg/ml of LF and 2.5 μg/ml of the antibody, the 5B13B1 antibody was found to be a potent neutralizing antibody, exhibiting a cell survival rate of about 87%, compared to the LB8 antibody, exhibiting a cell survival rate of less than 50%.

Immunoglobulins are divided into variable regions and constant regions. The variable regions direct the formation of antigen-antibody complexes by specifically recognizing epitopes on antigens. The constant regions, having mostly the same sequence between all the immunoglobulin classes, have effector functions, including activating the complement system, conferring an ability to pass across the placenta and acting as ligands for receptors on various immune cells. The specificity of an antibody to an antigen is determined by structural specificity according to the amino acid sequences of variable regions. Thus, based on the amino acid sequences of heavy chain and light chain variable regions, which were determined by those skilled in the art, various forms of recombinant antibodies may be prepared according to the intended use.

All types of recombinant antibodies, for example, chimeric antibodies, that are prepared in such a manner as to comprise a heavy chain variable region having the amino acid sequence represented by SEQ ID No. 2 and a light chain variable region having the amino acid sequence represented by SEQ ID No. 7, are included in the scope of the present invention. Herein, the antibody may be a whole antibody or a functional fragment of an antibody molecule.

The term “functional fragment of an antibody molecule”, as used herein, indicates a fragment retaining at least its antigen binding function, and includes Fab, F(ab'), $F(ab')_2$, scFv, and dsFv. Such antibody fragments may be obtained using proteolytic enzymes (e.g., a whole antibody is digested with papain to produce Fab fragments, and pepsin treatment results in the production of $F(ab')_2$ fragments), and may be preferably prepared by genetic recombinant techniques In a detailed embodiment of the present invention, a chimeric antibody was prepared by linking the heavy chain variable region of the 5B13B1 antibody, having the amino acid sequence of SEQ ID No. 2, to a human gamma 1 (γ1) heavy chain constant region, and the light chain variable region of the antibody, having the amino acid sequence of SEQ ID No. 7, to a human kappa (κ) light chain constant region. A vector expressing the chimeric antibody was designated “pdCMV-dhfrC-cLF Ab”. The chimeric antibody displayed antigen binding capacity similar to that of the murine 5B13B1 antibody.

Mouse-derived antibodies may induce undesired immune responses in humans because they are recognized as antigens in humans, and new human anti-mouse antibodies (HAMAs) against the mouse antibodies are produced. Many attempts have been made to overcome this problem by reducing the immunogenicity of non-human antibodies in humans. For this, the so-called humanization techniques are used. The initial preparation method of humanized antibodies is based on creating a chimeric antibody in which a constant region of human antibodies is conjugated to an antigen binding portion consisting of the whole antigen binding region of a non-human antibody. Such a chimeric antibody exhibits advantages of causing lower immune responses than murine antibodies and of having improved functionality. However, since chimeric antibodies still contain mouse variable regions, that Is, amino acid sequences of non-human variable regions, they cause HAMA responses when repeatedly administered to humans. In order to further humanize chimeric antibodies, many attempts have been made to recombine CDRs of murine monoclonal antibodies displaying antigen binding capacity with FRs of human antibodies, based on the concept that the recombination does not induce immune responses in humans but retains the antigen binding specificity and affinity of the murine antibodies (Jones P T et al., Nature, 1986, 4;321 (6069):522-5). Humanized antibodies prepared by CDR grafting, which is based on grafting CDR loops of murine antibodies onto human antibodies, contain much fewer non-human amino add sequences and thus have a reduced risk of HAMA responses compared to chimeric antibodies.

Thus, in another detailed aspect, the present invention relates to a humanized antibody specifically binding to anthrax toxin, comprising a humanized heavy chain variable region that includes complementarity determining regions (CDRs) derived from the heavy chain variable region of the 5B13B1 antibody and having the amino acid sequences represented by SEQ ID Nos. 3, 4 and 5 and a framework region (FR) derived from a heavy chain of a human antibody, and a humanized light chain variable region that includes CDRs derived from the light chain variable region of the 5B13B1 antibody and having the amino add sequences represented by SEQ ID Nos. 8, 9 and 10 and an FR derived from a light chain of a human antibody.

The term “humanized antibody”, as used herein, as described above, generally means an antibody that is non-immunogenic or has reduced immunogenicity in humans but retains the ability of its parent antibody to bind to its antigen. A humanized antibody is an antibody having an altered amino add sequence, and the amino acid sequence of the antibody may be reconstituted according to the intended purpose. The humanized antibody of the present invention, specifically binding to anthrax toxin, comprises a humanized heavy chain variable region and/or a humanized light chain variable region.

The term, “humanized heavy chain variable region”, as used herein, indicates a variable region that includes CDRs from the heavy chain variable region of the murine 5B13B1 antibody and an FR from a heavy chain of a human antibody. The term, “humanized light chain variable region”, as used herein, indicates a variable region that includes CDRs from the light chain variable region of the murine 5B13B1 antibody and an FR from a light chain of a human antibody. These humanized variable regions may be prepared using an ordinary genetic recombinant technique.

The term “complementarily determining regions (CDRs)” refers to amino acid sequences that determine the antigen binding affinity and specificity of a variable region. Three complementarity determining regions, CDR1, CDR2 and CDR3, are present in a variable region.

The term “framework regions (FRs)”, as used herein, refers to amino acid sequences that are interposed between CDRs. Such regions of an antibody serve to enable CDRs to bind an antigen in an appropriate orientation, and include FR1, FR2, FR3 and FR4.

The murine 5B13B1 antibody of the present invention was found to comprise the heavy chain variable region including a CDR1, having the amino add sequence of SEQ ID No. 3, a CDR2, having the amino add sequence of SEQ ID No. 4, and a CDR3, having the amino acid sequence of SEQ ID No. 5; and the light chain variable region including a CDR1, having the amino acid sequence of SEQ ID No. 8, a CDR2, having the amino acid sequence of SEQ ID No. 9, and a CDR3, having the amino acid sequence of SEQ ID No. 10.

A humanized heavy chain variable region may be created by recombining the CDRs of the heavy chain variable region of the 5B13B1 antibody, having the amino acid sequences of SEQ ID Nos. 3, 4 and 5, with FRs of a human antibody heavy chain. Also, a humanized light chain variable region may be created by recombining the CDRs of the light chain variable region of the 5B13B1 antibody, having the amino acid sequences of SEQ ID Nos. 8, 9 and 10, with FRs of a human antibody light chain.

The FRs of the heavy chain and light chain of human origin are not specifically limited, but the FRs of the human antibody heavy chain are preferably derived from gamma 1 ($\gamma 1$), gamma 2 ($\gamma 2$), gamma 3 ($\gamma 3$), gamma 4 ($\gamma 4$), mu ($\mu$), alpha 1 ($\alpha 1$), alpha 2 ($\alpha 2$), delta ($\delta$), or epsilon ($\epsilon$) types, and more preferably from the gamma 1 ($\gamma 1$) type. The FRs of the human antibody light chain are preferably derived from kappa ($\kappa$) or lambda ($\lambda$) types, and more preferably from the kappa ($\kappa$) type.

A humanized antibody comprising the humanized heavy chain variable region and/or the humanized light chain variable region may be a whole antibody or a functional fragment of an antibody molecule. Functional fragments of an antibody molecule include Fab, F(ab'), $F(ab')_2$, scFv, and dsFv.

Humanized antibodies induce reduced immune responses when applied to humans, compared to parent antibodies or chimeric antibodies.

In a further aspect, the present invention relates to a nucleotide sequence encoding a heavy chain variable region having the amino acid sequence represented by SEQ ID No. 2.

In yet another aspect, the present invention relates to a nucleotide sequence encoding a light chain variable region having the amino add sequence represented by SEQ ID No. 7.

Preferably, the heavy chain variable region having the amino add sequence represented by SEQ ID No. 2 has the nucleotide sequence of SEQ ID No. 1, and the light chain variable region having the amino add sequence represented by SEQ ID No. 7 has the nucleotide sequence of SEQ ID No. 6.

The nucleotide sequences of the heavy chain and light chain variable regions may be modified with one or more additions, deletions, or non-conservative or conservative substitutions of nucleotide bases.

The nucleotide sequences may be inserted into a vector for expression thereof.

In still another aspect, the present invention relates to a recombinant vector comprising the nucleotide sequence.

The term “recombinant vector”, as used herein, which describes a vector capable of expressing a protein of interest in a suitable host cell, refers to a genetic construct that comprises essential regulatory elements to which a gene insert is operably linked in such a manner as to be expressed in a host cell. The operable linkage to a recombinant vector may be prepared using a genetic recombinant technique well known in the art, and site-specific DNA cleavage and ligation may be easily achieved using enzymes generally known in the art.

The vector of the present invention includes, but is not limited to, plasmid vectors, cosmid vectors, bacteriophage vectors, and viral vectors. A suitable expression vector includes expression regulatory elements, such as a promoter, an operator, an initiation codon, a stop codon, a polyadenylation signal, and an enhancer, as well as signal sequences or leader sequences for membrane targeting or secretion. The promoter of the vector may be constitutive or inducible. An expression vector may also include a selectable marker that allows the selection of host cells containing the vector, and a replicable expression vector may include a replication origin.

The vector expressing an antibody or an antibody fragment may be a vector system that simultaneously expresses a light chain and a heavy chain in a single vector, or a system that expresses a light chain and a heavy chain in two separate vectors.

In still another aspect, the present invention relates to a transformant transformed with the vector.

The transformation includes any method by which nucleic acids can be introduced into organisms, cells, tissues or organs, and, as known in the art, may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, agitation with silicon carbide fiber, *agrobacterium*-mediated transformation, and PEG-, dextran sulfate- and lipofectamine-mediated transformation.

Host cells most suitable for objects may be selected and used because expression levels, modification, or the like of proteins vary depending on host cells. Host cells include, but are not limited to, prokaryotic cells such as *Escherichia coil, Bacillus subtilis, Streptomyces, Pseudomonas, Proteus mirabilis* or *Staphylococcus*. Also, eukaryotic cells useful as host cells include lower eukaryotic cells, such as fungi (e.g., *Aspergillus*) and yeasts (e.g., *Pichia pastoris, Saccharomyces cerevisiae, Schizosaccharomyces, Neurospora crassa*), and cells derived from higher eukaryotes, such as insect cells, plant cells and mammalian cells.

In still another aspect, the present invention relates to a method of preparing an antibody using the transformant.

An antibody may be prepared by cultivating the transformant under suitable conditions and recovering the antibody from the host cell culture (e.g., culture medium of the transformant).

The cultivation of host cells for antibody production may be performed under suitable culture conditions and using proper media, which are known in the art. This culturing process may be easily adapted according to the strains selected by those skilled in the art. Various culture methods are described in numerous literature (e.g., Biochemical Engineering, James M. Lee, Prentice-Hall International Editions, pp 138-176). An antibody produced may be purified using ordinary methods, which may be used separately or in combination, for example, dialysis, salting out (e.g., ammonium sulfate precipitation, sodium phosphate precipitation, etc.), ion exchange chromatography, size exclusion chromatography, and affinity chromatography.

In a further detailed aspect, the present invention relates to a monoclonal antibody specifically binding to anthrax toxin, which is produced by a hybridoma having accession number KCTC 10756BP.

The antibody produced by the hybridoma having accession number KCTC 10756BP is a novel neutralizing antibody, which has higher affinity than does the conventional LF8 antibody and displays preventive and therapeutic effects against anthrax through a neutralization mechanism different from that of the conventional LF8 antibody.

A hybridoma capable of producing an antibody specific to an antigen may be cultured on a large scale according to standard techniques. The monoclonal antibody produced by the aforementioned hybridoma may be used in an unpurified form, but may be preferably used after being purified using any method widely known in the art. The novel antibody of the present invention was purified by affinity chromatography using a Protein C column.

As described above, the amino acid sequences of the heavy chain and light chain variable regions of the 5B13B1 monoclonal antibody were identified. Thus, based on the amino acid sequences of the heavy chain and light chain variable regions of the 5B13B1 monoclonal antibody, those skilled in the art can construct various forms of recombinant antibodies according to the intended use. Also, since CDRs of the heavy chain and light chain were determined, based on the amino add sequences of the CDRs, those skilled in the art can construct various forms of recombinant antibodies according to the intended use.

In still another aspect, the present invention relates to a hybridoma having accession number KCTC 10756BP.

The hybridoma producing the 5B13B1 monoclonal antibody having the aforementioned properties was deposited under the Budapest Treaty at an international depositary authority, KCTC (Korean Collection for Type Cultures, Korean Research Institute of Bioscience and Biotechnology (KRIBB)), on Jan. 5, 2005 and assigned accession number KCTC 10756BP. The Korean Collection for Type Cultures, KCTC, is located at 52, Oun-dong, Yusong-Ku, Taejon 305-333, Republic of Korea.

In still another aspect, the present invention relates to a monoclonal antibody specifically recognizing the domain III of *Bacillus anthracis* lethal factor.

The 5B13B1 and 3C16B antibodies of the present invention are characterized by having therapeutic as well as preventive effects against anthrax because they are able to bind to lethal factor (LF) of *B. anthracis* and also to lethal toxin (LeTx). Such a feature of antibodies is imparted according to epitopes on antigens, which are responsible for antigen binding affinity of antibodies. An epitope on LF, to which the present antibodies are bound, does not participate in the binding of LF to protective antigen (PA), or its ability to bind the antibodies is not interrupted by the binding of PA thereto. For this reason, the present antibodies retain their binding capacity to LF even when LF binds to PA to form LeTx, and thus have therapeutic efficacy against anthrax.

To determine an epitope on *Bacillus anthracis* lethal factor, responsible for the aforementioned feature of the present antibodies, the present inventors constructed deletion mutants of the LF antigen and conducted slot blot analysis to determine an epitope on the antigen, participating in the binding to the antibodies. As a result, the present antibodies were found to recognize the domain III, which is located at amino add positions 303 to 383 of the LF of *B. anthracis*. In particular, a peptide represented by SEQ ID No. 39, corresponding to amino add positions 347 to 365, has high binding affinity to the present antibodies.

That is, the present invention is greatly meaningful in terms of identifying an epitope on the LF of *B. anthracis*, which provides preventive and therapeutic effects against anthrax. When the epitope is used as an antigen, those skilled in the art can construct an antibody that acts through the same neutralization mechanism as in the antibodies of the present invention.

Thus, the present invention provides a monoclonal antibody specifically recognizing the domain III of *Bacillus anthracis* lethal factor, and more preferably a monoclonal antibody specifically recognizing the domain III of *Bacillus anthracis* lethal factor, the domain III having the amino acid sequence of SEQ ID No. 42.

In still another aspect, the present invention relates to a composition for neutralizing anthrax toxin, comprising the aforementioned antibody.

The present antibodies may be useful as preventive as well as therapeutic agents for anthrax because they exhibit a potent neutralizing effect against anthrax toxin. When the antibodies were administered to cells before and after toxin challenge (the time point at which toxin was administered was designated "0"), namely at time points of −60, −30, 0, 5 and 15 min, in order to examine cell viability according to the administration time of the antibodies, the antibodies acted effectively when administered after as well as before exposure to anthrax toxin. The 5B13B1 antibody was evaluated for In vivo toxin-neutralizing activity using Fisher 344 rats. As a result, an antibody control group (receiving only antibody) and a test group (receiving both antibody and toxin) all survived for a period of 3 days, but all rats of a toxin control group (receiving only toxin) died within average 68 min. Also, all four rats of an antibody group, to which the antibody was administered 5 min after anthrax toxin injection, survived for the test period, and another antibody group, to which the antibody was administered 15 min after anthrax toxin injection, displayed a 50% survival rate.

The present composition may be provide for preventing and treating anthrax in humans, as well as in anthrax infection-susceptible livestock, such as cows, horses, sheep, swine, goats, camels, and antelopes.

The term "prevention", as used herein, means all activities that inhibit or delay the incidence of anthrax through the administration of a composition comprising the present antibody. The term "treatment", as used herein, refers to all activities that alleviate and beneficially affect anthrax symptoms through the administration of the present antibody.

When used as a therapeutic antibody, the present antibodies may be linked to a known therapeutic agent by direct or indirect coupling (e.g., covalent bonding) through a linker, and administered to the body in antibody-therapeutic agent conjugates in order to prevent or treat anthrax. Available therapeutic agents include chemical therapeutic agents, radionuclides, immunotherapeutic agents, cytokines, chemokines, toxins, biological agents, and enzyme inhibitors. Effective therapeutic agents may have enhanced efficacy when they are administered with an antibody that is highly specific to an antigen so as to remain at high concentrations at an infection site.

The composition comprising the antibody according to the present invention may include a pharmaceutically acceptable carrier.

The antibody composition includes an acceptable carrier and is formulated into a suitable dosage form according to administration modes. Pharmaceutical preparations suitable for administration modes are known, and generally include surfactants that facilitate transport across the membrane. Such surfactants may be derived from steroids, or may be cationic lipids such as N-[1-(2,3-dioleyloxy)propyl]-N,N,N-trimethylammonium chloride (DOTMA), or various compounds such as cholesterol hemisuccinate and phosphatidyl glycerol.

For oral administration, the pharmaceutical composition may be presented as discrete units, for example, capsules or tablets; powders or granules; solutions, syrups or suspensions (edible foam or whip formulations in aqueous or non-aqueous liquids); or emulsions.

For parenteral administration, the pharmaceutical composition may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients available for use in injectable solutions include, for example, water, alcohol, polyols, glycerin, and vegetable oils. Such a composition may be presented in unit-dose (single dose) or multiple dose (several doses) containers, for example, sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical composition of the present invention may include antiseptics, solubilizers, stabilizers, wetting agents, emulsifiers, sweeteners, colorants, odorants, salts (the material of the present invention may be provided in a pharmaceutically acceptable salt form), buffering agents, coating agents, or anti-oxidants.

If desired, the present composition, in addition to the material of the present invention, may contain a therapeutically active agent.

The present composition may be formulated into dosage forms for use in humans or veterinary use.

In still another aspect, the present invention relates to a method of preventing or treating anthrax by administering the aforementioned antibody.

The composition comprising the antibody may be administered to *B. anthracis*-infected or highly susceptible humans and livestock, such as cows, horses, sheep, swine, goats, camels, and antelopes, in order to prevent or treat the incidence of anthrax. When a subject is already infected, the present antibody may be administered alone or in combination with an antibiotic or another antimicrobial treatment.

The antibody composition of the present invention may be administered in a pharmaceutically effective amount in a single- or multiple-dose. The pharmaceutical composition of the present invention may be administered via any of the common routes, as long as it is able to reach the desired tissue. Thus, the present composition may be administered via oral or pareteral (e.g., subcutaneous, intramuscular, intravenous, or intradermal administration) routes, and may be formulated into various dosage forms. A preferred formulation is an injectable preparation. Intravenous, subcutaneous, intradermal, intramuscular and dropping injectable preparations are possible.

The antibody composition of the present invention may be administered in a pharmaceutically effective amount The term "pharmaceutically effective amount", as used herein, refers to an amount sufficient for treating or preventing diseases, which is commensurate with a reasonable benefit/risk ratio applicable for medical treatment or prevention. An effective dosage amount of the composition may be determined depending on the severity of the illness, drug activity, the patient's age, weight, health state, gender and drug sensitivity, administration routes, drugs used in combination with the composition; and other factors known in medicine, and may be readily determined by those skilled in the art The antibody composition of the present invention may be administered as a sole therapeutic agent or in combination with other therapeutic agents, and may be administered sequentially or simultaneously with conventional therapeutic agents. This administration may be provided in single or multiple doses.

In still another aspect, the present invention relates to a kit for detecting anthrax toxin, comprising the aforementioned antibody.

With the kit comprising the antibody, anthrax infection may be easily and simply diagnosed by detecting anthrax toxin, specifically recognized by the monoclonal antibody, in a biological sample. Anthrax infection may be diagnosed by reacting a biological sample with the present antibody and detecting antigen-antibody complex formation.

The term "biological sample", as used herein, includes, but is not limited to, samples allowing the detection of anthrax toxin, such as tissues, cells, whole blood, serum, plasma, cerebrospinal fluid, urine, saliva, or the like. These biological samples may be reacted with the antibodies of the present invention in the form of being manipulated or not so as to identify *Bacillus anthracis* infection.

The term "detection of anthrax toxin", as used herein, refers to the identification of the presence and amount of anthrax toxin, and in particular lethal factor (LF) and/or lethal toxin (LeTx), by quantitatively or qualitatively measuring the signal size of a detection label bound to antigen-antibody complexes.

Such a detection kit includes the monoclonal antibody of the present invention, as well as tools, reagents, and the like, which are generally used in the art for immunological analysis. These tools/reagents include, but are not limited to, suitable carriers, labeling substances capable of generating detectable signals, solubilizing agents, detergents, buffering agents and stabilizing agents. When the labeling substance is an enzyme, the kit may include a substrate allowing the measurement of enzyme activity and a reaction terminator. Suitable carriers include, but are not limited to, soluble carriers, for example, physiologically acceptable buffers known in the art, for example, PBS, insoluble carriers, for example polymers such as polystylene, polyethylene, polypropylene, polyesters, polyacrylnitrile, fluorocarbon resin, crosslinked dextran, polysaccharides and magnetic microparticles composed of latex plated with metals, papers, glass, metals, agarose, and combinations thereof.

Antigen-antibody complex formation may be detected by using histoimmunological staining, radio-immunoassay (RIA), enzyme-linked immunosorbent assay (ELISA), Western blotting, immunoprecipitation assay, immunodiffusion assay, complement fixation assay, FACS and protein chips, but the present invention is not limited to these examples.

Labels enabling the quantitative or qualitative measurement of the formation of antigen-antibody complexes include, but are not limited to, enzymes, fluorescent substances, ligands, luminescent substances, microparticles, redox molecules and radioactive isotopes. Examples of enzymes available as detection labels include, but are not limited to, β-glucuronidase, β-D-glucosidase, β-D-galactosidase, urase, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescin, isothiocyanate, rhodamine, phycoerythrin, phycocyanin, allophycocyanin, o-phthaldehyde and fluorescamin. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_{8+}$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

A better understanding of the present invention may be obtained through the following examples which are set forth to illustrate, but are not to be construed as the limit of the present invention.

EXAMPLE 1

Preparation and Production of Toxin Antigens

1. Construction of Plasmids Expressing Toxin Antigens

The *Bacillus anthracis* pXO1 plasmid carrying the genes coding for protective antigen and lethal factor and a pT7-PA plasmid carrying the protective antigen gene were obtained from the Pathogen Control Laboratory, the Korean Center for Disease Control and Prevention. The protective antigen gene was excised from the pT7-PA plasmid by digestion with BamHI and SalI, and inserted into a pBS1-1 vector, thus yielding an expression vector. Separately, the lethal factor gene was amplified by polymerase chain reaction (PCR) using the *B. anthracis* pXO1 plasmid as a template with a pair of primers, represented by SEQ ID Nos. 11 and 12, and cloned into pBS1-1 containing an S1-tag, which was obtained from Aprogen Inc., Korea (Meesook et al., J Immunol Methods. 2003 December; 283(1-2):77-89) (FIG. 1).

```
                                        (SEQ ID No. 11)
5'-primer: 5'-cgtggatccatggcgggcggtcatggtgatg-3'

                                        (SEQ ID No. 12)
3'-primer: 5'-gattctagattatgagttaataatgaac-3'
```

2. Production and Purification of Toxin Antigens

To express PA and LF in bacteria, *E. coli* HB2151 was transformed with each of the constructed plasmids, cultured in 2×YT medium, and treated with 1 mM IPTG (isopropyl-β-D-thiogalactopyranoside) to induce protein expression. *E. coli* cells were then harvested by centrifugation, resuspended in 1×TES (0.2 M Tris-Cl, 0.5 mM EDTA, 0.5 M sucrose, pH 8.0), and lysed with ⅕×TES. After the cell lysate was centrifuged, the supernatant was recovered, passed through a 0.22-μm filter, and subjected to affinity chromatography using a Sepharose column (Aprogen) to which an antibody to S1-tag, AP1, was bound.

Figure 2:
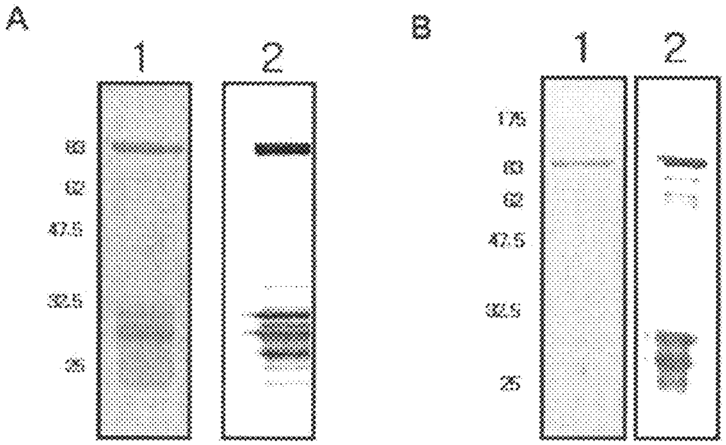
FIG. 2 shows the results of SDS-PAGE (1) and Western blotting (2) of protective antigen (A) and lethal factor (B) expressed in *E. coli;*

The column was loaded with the protein sample (supernatant), and washed with 0.5 M NaCl in 0.1 M Tris-Cl (pH 8.0). The bound protein was then eluted with 0.2 M Glycin-HCl (pH 2.7). The eluted protein was immediately neutralized with 0.1 M Tris-Cl (pH 9.0) and dialyzed in phosphate buffer. The protein was then treated with thrombin (1 U/100 μg of fusion protein) for 2 hrs to remove the S1-tag therefrom, equilibrated with phosphate buffer, and purified by fast protein liquid chromatography using a Superose 6 column (gel filtration). Fractions containing the toxin protein were collected. After the amount of protein was determined, the purified protein was analyzed using SDS-PAGE and Western blotting (FIG. 2).

EXAMPLE 2

Establishment of Mouse Hybridomas

1. Mouse Immunization with Protective Antigen of *Bacillus anthracis*

Balb/c mice were immunized with the purified lethal factor of *B. anthracis* by subcutaneous injection. Mice were immunized first with 20 μg of the lethal factor emulsified in complete Freund's adjuvant, and were then immunized with 20 μg of the lethal factor emulsified in incomplete Freund's adjuvant three times more, once every two weeks. After two weeks, the lethal factor was diluted with phosphate buffer and intravenously injected into mice.

2. Evaluation of Polyclonal Antibodies in sera for Anthrax-Neutralizing Activity After Immunization Injection After the second immunization, blood samples were collected from orbital venous plexus of mice, and isolated sera were assessed for anthrax toxin-neutralizing activity. A neutralization assay was carried out using a mouse macrophage cell line, J774A.1. 4×10$^4$ J774A.1 Cells were seeded onto a 96-well cell culture plate, and cultured for 18 hrs. The protective antigen and lethal factor were added to each well in final concentrations of 400 ng/ml and 200 ng/ml, respectively. An antiserum against the lethal factor was applied to cells after being serially diluted and pre-incubated with the toxin antigen.

Figures 3, 4:
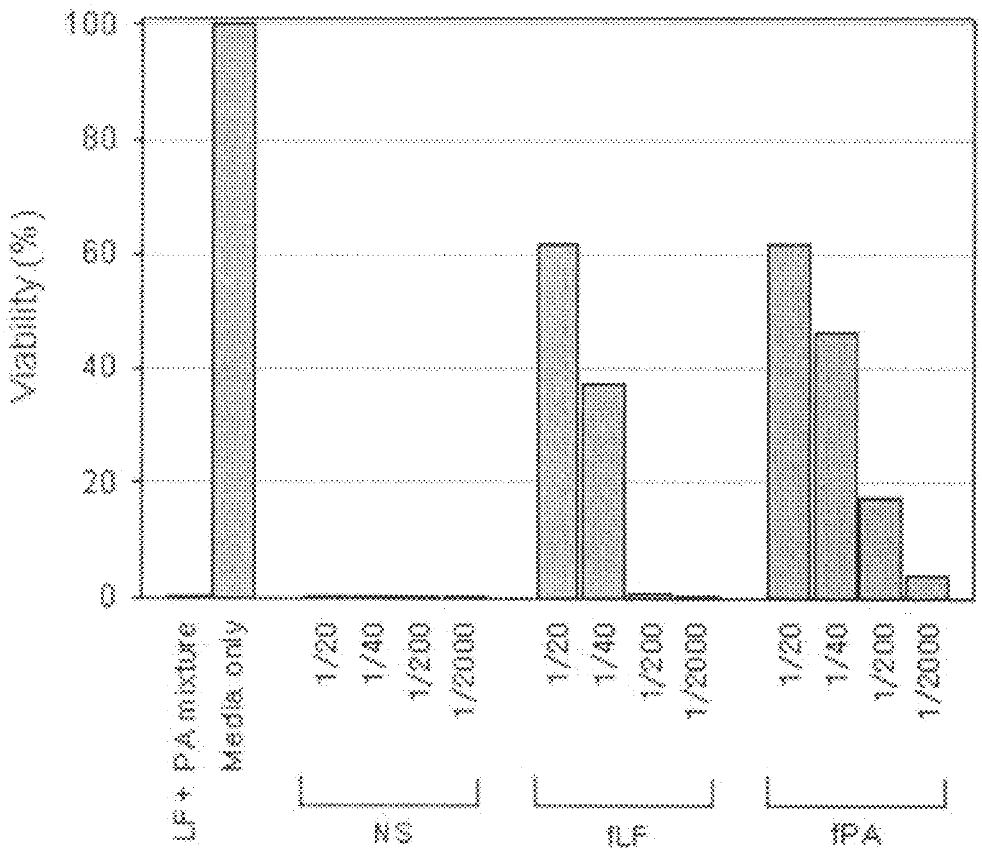
FIG. 3 shows the results of a neutralization assay for sera obtained from mice immunized with lethal factor (fLF) and protective antigen (fPA), using a murine macrophage cell line.
FIG. 4 shows the results of Western blotting for detecting the binding of an antibody according to the present invention, 5B13B1, to lethal factor.

After incubation for 3 hrs, MTT (3-(4,5-dimethylthiazol-2-yl)-2,5-diphenyl tetrazolium bromide) was added to each well in a final concentration of 1.5 mg/ml, followed by incubation for 1 hr. After the culture medium was then removed, dimethyl sulfoxide (DMSO) was added to each well, and absorbance was measured at 540 nm to determine cell viability. Cell viability was expressed as relative viability, in which cell viability in the presence of anthrax toxin alone was designated "0%" and the viability of cells not treated with the toxin was designated "100%" (FIG. 3).

A 1/20 dilution of antisera was found to inhibit cell death owing to the action of anthrax toxin by about 60%. Also, a 1/20 dilution of antisera against another protein of anthrax toxin, protective antigen, exhibited a roughly 60% neutralizing activity.

3. Establishment of Mouse Hybridomas Producing Monoclonal Antibodies

After the immunized mice were sacrificed, the spleens were excised from the mice. Splenocytes were extracted and fused with mouse myeloma F0 cells. Then, fused cells were selected using HAT medium. The fused cells were cultured in 96-well cell culture plates, and the cell culture fluids were assessed using ELISA to select cells specifically responding to the protective antigen.

Cell culture fluids, which were found to bind to lethal factor, were analyzed using a neutralization assay for anthrax toxin according to the same procedure as in Example <2-2> to determine cells having toxin-neutralizing activity. Cells having anthrax toxin-neutralizing activity by specifically binding to lethal factor were subcloned using limiting dilution. Finally, two monoclonal antibodies against lethal factor, 5B13B1 and 3C16C3, which were able to neutralize anthrax toxin, were selected, and the results are given in Table 1, below. The reactivity of the antibodies against lethal factor was analyzed by ELISA as well as Western blotting (FIG. 4).

TABLE 1

LF-binding activity and anthrax toxin-neutralizing activity of the selected monoclonal antibodies

| Antibody | LF-binding activity[a] (Abs. at 490 nm) | LeTx-neutralizing activity[b] (Survival rate, %) |
|---|---|---|
| 5B13B1 | 1.517 | 99.7 |
| 3C16C3 | 1.72 | 104.3 |

[a]LF-binding activity determined by ELISA
[b]LeTx-neutralizing activity determined by in vitro cytotoxicity assay 4. Production and Purification of Monoclonal Antibodies The selected hybridomas were cultured in DMEM medium supplemented with 10% FBS and streptomycin-penicillin, and the FBS concentration decreased to 5% and then 2%. After cells were finally adapted for growth in serum-free medium, they were cultured in serum-free medium. The culture fluids were recovered, and subjected to Protein G affinity chromatography to purify monoclonal antibodies contained in the culture fluids.

EXAMPLE 3

Evaluation of Toxin-Neutralizing Activity of the Monoclonal Antibodies

1. Evaluation of Antigen Binding Ability of the Monoclonal Antibodies

The selected monoclonal antibodies were evaluated for antigen binding activity using surface plasmon resonance with a BiaCoreX instrument. The expressed lethal factor was immobilized onto a CM5 chip and reacted with serial dilutions of the antibody. As a result, the 5B13B1 antibody was found to have a $K_{on}$ value of $4.34\times10^4\ M^{-1}S^{-1}$ and a $K_{off}$ of $1.14\times10^{-4}S^{-1}$. From these $K_{on}$ and $K_{off}$ values, a $K_d$ of 2.2 nM was calculated, indicating that the 5B13B1 antibody has a high affinity to its antigen (FIG. 5).

2. Evaluation of Toxin-Neutralizing Activity at the Cell Level

The two selected monoclonal antibodies against lethal factor were serially diluted and analyzed for anthrax toxin-neutralizing activity using a mouse macrophage cell line, J774A.1. Each antibody was serially diluted, reacted with anthrax toxin at 4° C. for 30 min, and applied to the cell line. A neutralization assay for anthrax toxin was carried out according to the same method as in Example <2-2>. As a result, the monoclonal antibodies were found to protect cells against anthrax toxin by inhibiting the action of the toxin in a dose-dependent manner.

Figure 6:
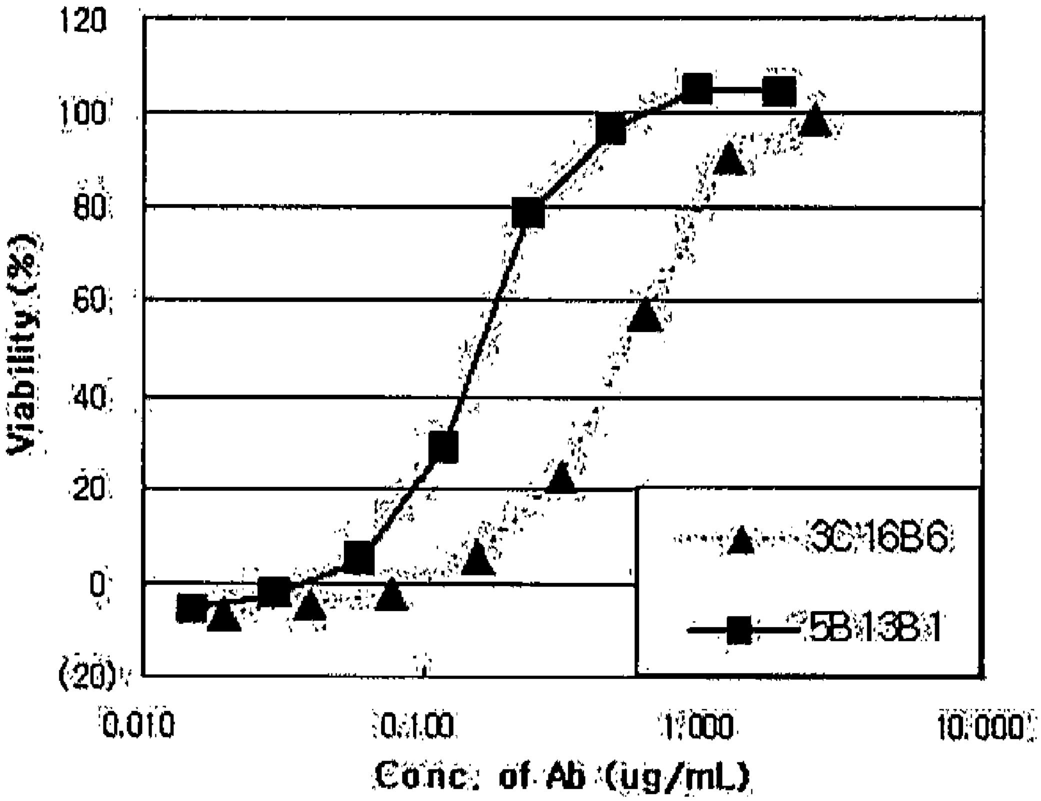
FIG. 6 shows the results of a neutralization assay using a murine macrophage cell line for detecting the anthrax toxin-neutralizing activity of purified 5B13B1 and 3C16C3 antibodies.

When cells were exposed to 400 μg/ml of protective antigen and 200 μg/ml of lethal factor, the concentrations of the antibodies that protect 50% of the cells, $IC_{50}$, were calculated. The 5B13B1 antibody displayed an $IC_{50}$ of 0.212 μg/ml, and the 3C16C3 antibody showed an $IC_{50}$ of 0.604 μg/ml. The 5B13B1 antibody was found to have potent neutralizing activity because about 0.64 antibody molecules per lethal factor molecule resulted in 50% inhibition of toxin action (FIG. 6).

Figure 7:
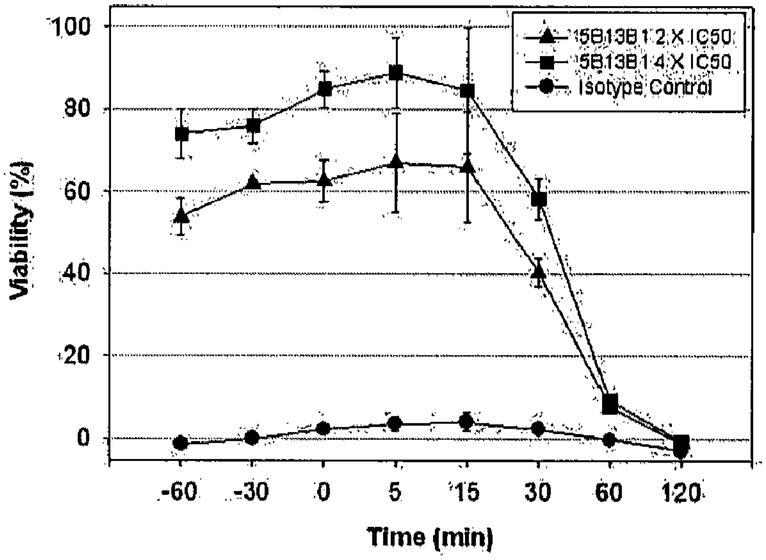
FIG. 7 shows the results of a neutralization assay using a murine macrophage cell line according to antibody administration time for evaluating the preventive and therapeutic effects of the 5B13B1 antibody.

Based on the above results, cell viability was examined according to the administration time of the antibodies. The time point at which toxin was administered was designated "0", and each antibody was applied to cells at time points of −60, −30, 0, 5, 15, 30, 60 and 120 min. A concentration of the 5B13B1 antibody four times $IC_{50}$ displayed a roughly 80% neutralizing activity when administered at time points of −60, −30, 0, 5 and 15 min. Such a neutralizing activity decreased to roughly 60% and roughly 10% when the antibody was applied 30 min and 60 min after toxin challenge, and was almost lost when the antibody was applied 120 min after toxin challenge. These results, in which the monoclonal antibodies effectively neutralized anthrax toxin after as well as before exposure to the toxin, indicate that these antibodies are potentially useful as therapeutic and preventive agents for anthrax toxin (FIG. 7).

3. Evaluation of in vivo Toxin-Neutralizing Activity using Rats

The 5B13B1 antibody was evaluated for in vivo toxin-neutralizing activity using an in vivo neutralization assay using Fisher 344 rats. 80 μg of protective antigen and 40 μg of lethal factor, which cause the death of rats within 100 min, were dissolved in 200 μl of phosphate buffer and injected into the tail vein of rats. 42.2 μg of the 5B13B1 antibody was pre-incubated with the toxin antigens (PA and LF) and injected into rats. The amount of the antibody used was determined based on a concentration that protected 100% of cells in the toxin-neutralizing assay using the murine macrophage cell line.

Figure 8:
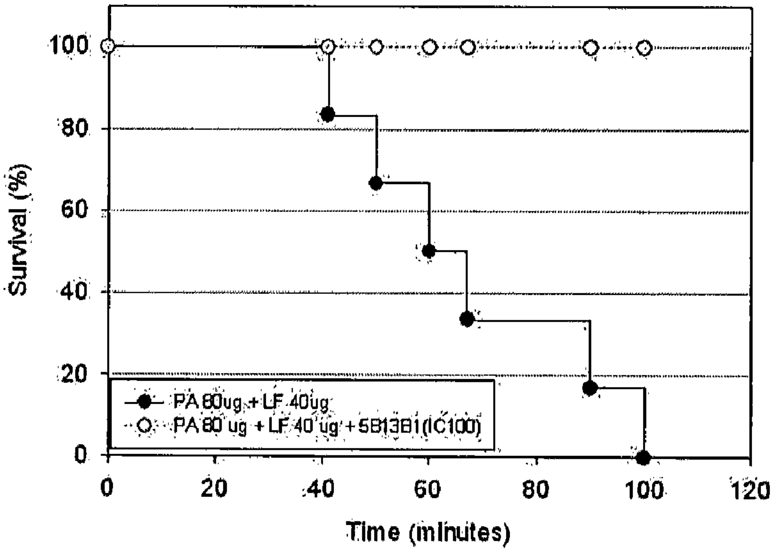
FIG. 8 shows the results of the evaluation of in vivo toxin-neutralizing activity of the 5B13B1 antibody in Fisher rats as an animal model.

A control group was administered with the toxin alone, an antibody control group with the antibody alone, and a test group with both the toxin and the antibody. Each group consisted of six rats. The six rats in the antibody control group and the test group all survived for a period of 3 days. In contrast, toxin control rats were all killed within 100 min, with an average time to death of 68±22 min. These results indicate that the present antibodies are capable of effectively neutralizing anthrax toxin in vivo (FIG. 8).

4. Evaluation of Toxin-Neutralizing Activity of the Monoclonal Antibodies After Injection with Anthrax Lethal Toxin.

In order to determine whether the antibodies have a therapeutic effect after infection with *B. anthracis*, an in vivo neutralization assay against anthrax toxin was performed. After the anthrax toxin was injected into rats, the 5B13B1 antibody was injected into the rats. 80 μg of protective antigen and 40 μg of lethal factor were dissolved in 200 μl of phosphate buffer and injected into the tail vein of rats. After 5, 15 and 30 min, 42.2 μg of the 5B13B1 antibody were injected into the rats through the tail vein, and the rats were monitored for survival for a period of three days.

Figure 9:
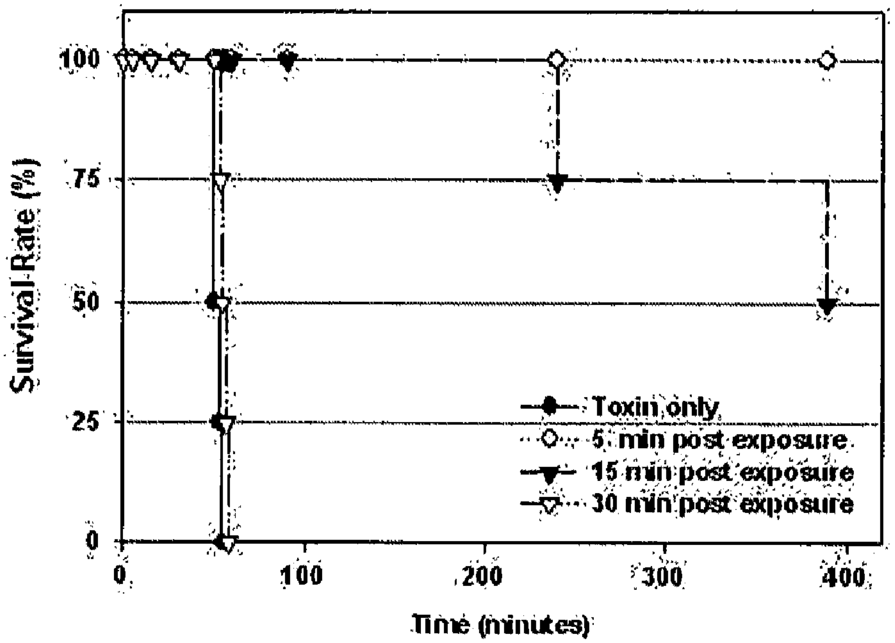
FIG. 9 shows the therapeutic effect of 5B13B1 antibody when the antibody was injected into Fisher rats into which anthrax toxin had been injected.

All four rats in a toxin control group died an average of 52 min after the toxin challenge. All four rats survived for the test period when receiving the antibody 5 min after the toxin challenge. When the antibody was administered to rats 15 min after the toxin challenge, 50% of the rats survived, and the average time to death was 314 min. All rats that received the antibody 30 min after exposure to the toxin died, and the time to death, which was an average of 55 min, was similar to that of the toxin control group (FIG. 9).

EXAMPLE 4

Identification of the Neutralization Mechanism of the Novel 5B13B1 Monoclonal Antibody 1. Identification of the Neutralization Mechanism of the Monoclonal Antibody To identify the neutralization mechanism of the antibody, the 5B13B1 antibody was evaluated for whether it inhibited the binding of protective antigen and lethal factor. Trypsin was reacted with the purified protective antigen at a ratio of 1:1000 at room temperature for 20 min, and the reaction was terminated by the addition of soybean trypsin inhibitor. The activated $[PA63]_7$ was purified through Mono Q anion-exchange chromatography (Pharmarcia). The purified $[PA63]_7$ was dialyzed in 20 mM Tris (pH 8.0), and 2 μg of the purified $[PA63]_7$ was then reacted with 4 μg of lethal factor at room temperature for 1 hr. The 5B13B1 antibody or an irrelevant antibody (anti-angiopoietin 2) was added to the reaction solution in an amount equal to the amount of lethal factor. The resulting reaction mixture was electrophoresed on a 4-15% native gel.

Figure 10:
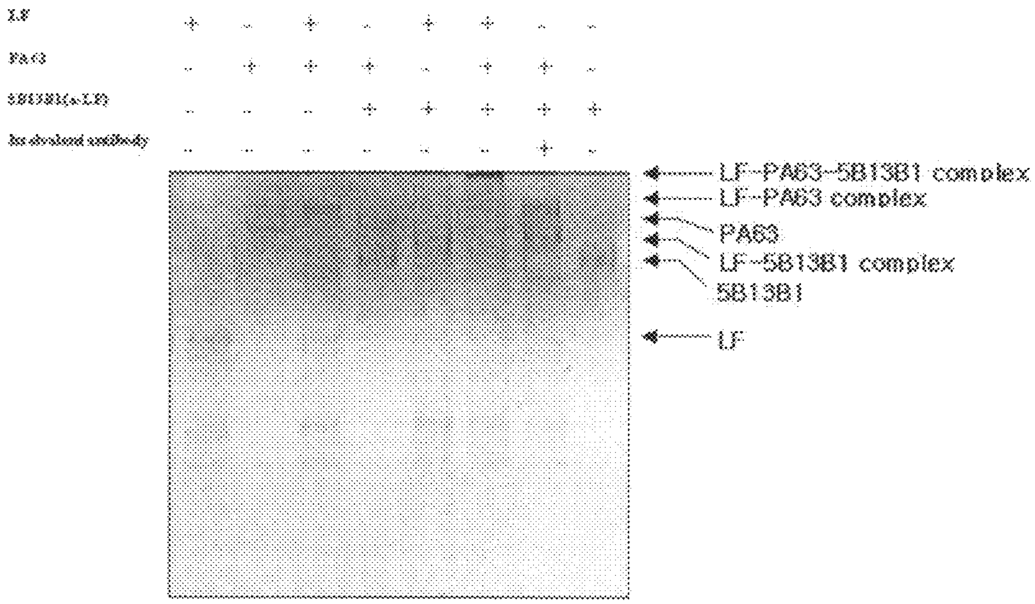
FIG. 10 shows the results of the evaluation to determine whether the 5B13B1 antibody inhibits the binding of protective antigen and lethal factor.
Figure 11:
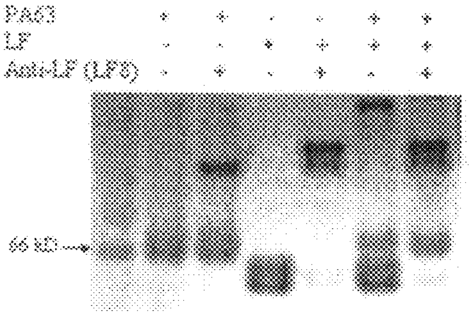
FIG. 11 shows the ability of conventional LF8 antibody to inhibit the binding of protective antigen and lethal factor.

As shown in FIG. 10, when the reaction proceeded in the presence of all of the 5B13B1 antibody, the lethal factor (LF) and the protective antigen (PA), the three components together formed tertiary complexes having a high molecular weight In contrast, when an irrelevant antibody was used, the normal PA-LF complexes were formed. These results indicate that the neutralization mechanism of the present antibodies does not involve directly inhibiting the binding of PA and LF. A previously reported LF-neutralizing antibody, LF8, was tested according to the same method. As a result, the LF8 antibody was found to interrupt the formation of lethal toxin by inhibiting the binding of PA and LF (FIG. 11).

Figure 12:
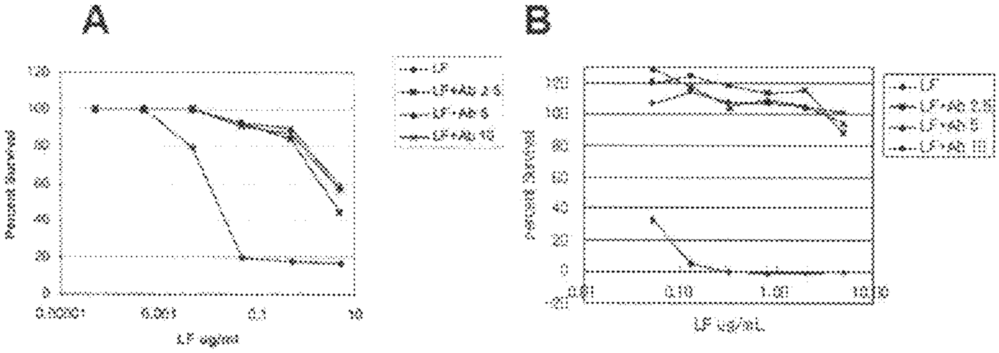
FIG. 12 shows the results of comparison of neutralizing capacity of the conventional LF8 antibody (A) and the novel 5B13B1 antibody (B) at the cell level.

That is, the LF8 antibody inhibits the binding of PA and LF by binding near the PA-binding domain of LF. In contrast, since the 5B13B1 antibody binds to a region other than the PA-binding domain of LF, it has the ability to bind to both LF and lethal toxin. Thus, the neutralization mechanisms of the two antibodies were considered distinctly different 2. Evaluation of Neutralizing Activity of the Monoclonal Antibody at the Cell Level A neutralization assay was performed in cells according to the same method as in Example <2-2>. The 5B13B1 antibody was found to have a higher neutralizing activity than the LF8 antibody. When cells were exposed to 5 μg/ml of LF, the 5B13B1 antibody of 2.5 μg/ml protected about 87% of the cells, but the LF8 antibody protected less than 50% of the cells (FIG. 12).

EXAMPLE 5

Analysis of Amino Acid Sequences and Nucleotide Sequences and Determination of CDRs of the Heavy Chain and Light Chain Variable Regions of the 5B13B1 Antibody 1. Analysis of Nucleotide Sequences of the Heavy Chain and Light Chain Variable Regions of the Antibody To determine nucleotide sequences of the heavy chain and light chain variable regions of the antibody, total RNA was isolated from a mouse hybridoma expressing the 5B13B1 antibody using an RNA extraction kit. The isolated total RNA was reverse transcribed by RT-PCR to synthesize cDNA. Using the synthesized cDNA, PCR was carried out with a pair of primers of SEQ ID Nos. 13 and 14 for amplifying the heavy chain variable region, and with a pair of primers of SEQ ID Nos. 15 and 16 for amplifying the light chain variable region. PCR conditions included 30 cycles of 1 min at 94° C., 30 sec at 60° C. and 1 min at 72° C. As a result, a 480-bp DNA fragment, which was the heavy chain variable region, and a 410-bp DNA fragment, which was the light chain variable region, were amplified. Each DNA fragment was cloned into a pGEM-T Easy vector (Promega), and subjected to DNA sequencing analysis to determine the DNA sequences of the heavy chain and light chain variable regions. Since in the determined sequence, the primer of SEQ ID No. 13 for the heavy chain variable region and the primer of SEQ ID No. 15 for the light chain variable region consisted of variable sequences, the N-terminal sequence of the 5B13B1 antibody was determined using a protein sequence analyzer in order to normalize the upstream amino acid sequences of the variable regions. As a result, the first amino add residue of the heavy chain variable region was found to be glutamate (Glu), and the first and second amino add residues of the light chain variable region were found to be glutamate (Glu) and asparagine (Asn). Thus, to construct accurate heavy chain and light chain variable regions, PCR was carried out using the pGEM-T easy vector carrying the genes coding for the heavy chain and light chain variable regions, with a pair of primers, represented by SEQ ID Nos. 17 and 18, for amplifying the heavy chain variable region, and a pair of primers, represented by SEQ ID Nos. 19 and 20, for amplifying the light chain variable region. As a result, a 362-bp DNA fragment of SEQ ID No. 2, containing the heavy chain variable region and the primers, and a 341-bp DNA fragment of SEQ ID No. 7, containing the light chain variable region and the primers, were amplified, and cloned into a pGEM-T easy vector. Nucleotide sequences of the heavy chain and light chain variable regions were analyzed using a DNA sequencer.

2. Determination of CDRs of the Heavy Chain and Light Chain Variable Regions

The CDRs of the heavy chain and light chain variable regions were determined using a method available from an Internet site, http://www.bioinf.org.uk/abs/seqtest.html, and an antibody sequence was tested against the Kabat sequence database (FIGS. 13 and 14).

EXAMPLE 6

Construction of Chimeric Antibody and Evaluation of Antigen Binding Capacity Thereof for Confirmation of the Antibody Gene 1. Construction of Chimeric Antibody and Expression Vector Thereof In order to confirm whether the antibody gene obtained In the present invention codes for an antibody recognizing and binding to anthrax toxin, a recombinant antibody in a chimeric form was constructed and evaluated for antigen binding capacity. For the construction of a chimeric antibody, first, heavy chain and light chain leader sequences were obtained by PCR, which was carried out using a pdCMV-dhfrC-3E8 vector with a pair of primers of SEQ ID Nos. 21 and 22 for the heavy chain leader sequence and a pair of primers of SEQ ID Nos. 23 and 24 for the light chain leader sequence. As a result, an 87-bp DNA fragment for the heavy chain and a 92-bp DNA fragment for the light chain were obtained. For amplifying heavy chain and light chain variable regions, PCR was carried out using the pGEM-T easy vector carrying the genes coding for the heavy chain and light chain variable regions, with a pair of primers, represented by SEQ ID Nos. 17 and 18, for amplifying the heavy chain variable region, and a pair of primers, represented by SEQ ID Nos. 19 and 20, for amplifying the light chain variable region. As a result, a 362-bp DNA fragment of SEQ ID No. 2, containing the heavy chain variable region and the primers, and a 341-bp DNA fragment of SEQ ID No. 7, containing the light chain variable region and the primers, were obtained. The DNA fragments thus obtained were subjected to recombinant PCR using a pair of primers of SEQ ID Nos. 21 and 18 for obtaining a heavy chain, and a pair of primers of SEQ ID Nos. 23 and 20 for obtaining a light chain. As a result, a 434-bp DNA fragment, corresponding to a heavy chain, and a 415-bp DNA fragment, corresponding to a light chain, were obtained. To construct an expression vector for the heavy chain and light chain, first, the DNA fragment containing the heavy chain leader sequence (SEQ ID No. 25) and variable region was digested with EcoRI and ApaI, and ligated into the same restriction enzyme sites of the pdCMV-dhfrC vector, carrying human heavy chain and light chain constant region sequences. The heavy chain sequence was confirmed using a DNA sequencer. Another DNA fragment containing the light chain leader sequence (SEQ ID No. 26) and variable region was digested with HindIII and BsiWI, and ligated into the same restriction enzyme sites of the vector into which a heavy chain gene was already cloned. The light chain sequence was confirmed using a DNA sequencer. The finally constructed expression vector was designated "pdCMV-dhfrC-cLF Ab".

2. Expression of the Chimeric Antibody and Evaluation of Antigen Binding Capacity Thereof In order to directly express the chimeric antibody in cells, the expression vector was transformed into an animal cell line.

In detail, COS7 cells were subcultured in DMEM medium (GIBCO) supplemented with 10% fetal bovine serum in an incubator at 37° C. under 5% $CO_2$. The cells were plated on a 100-mm culture dish at a density of $1\times10^6$ cells/ml, cultured at 37° C. overnight, and washed with OPTI-MEM I (GIBCO) three times. Separately, 5 μg of the pdCMV-dhfrC-cLF Ab vector prepared in Example 6-1 was diluted with 800 μl of OPTI-MEM I, and 50 μl of lipofectamine (GIBCO) was also diluted with 800 μl of OPTI-MEM I. The two dilutions were mixed in a 15-ml tube and incubated at room temperature for more than 15 min in order to form DNA-lipofectamine complexes. The DNA-lipofectamine mixture was supplemented with 6.4 ml of OPTI-MEM I and poured onto the washed COS7 cells, and the plates were gently swirled. Transformation was allowed by incubating the cells in the culture medium containing the DNA-lipofectamine mixture in an incubator at 37° C. under 5% $CO_2$ for 48 hrs. The culture fluid was recovered, and its antibody concentration was determined using sandwich ELISA. For sandwich ELISA, the whole LF protein was used as a capture substance, and anti-human and anti-mouse antibodies (Fc-specific, Sigma), conjugated to horseradish peroxidase, were used as secondary antibodies.

Figure 15:
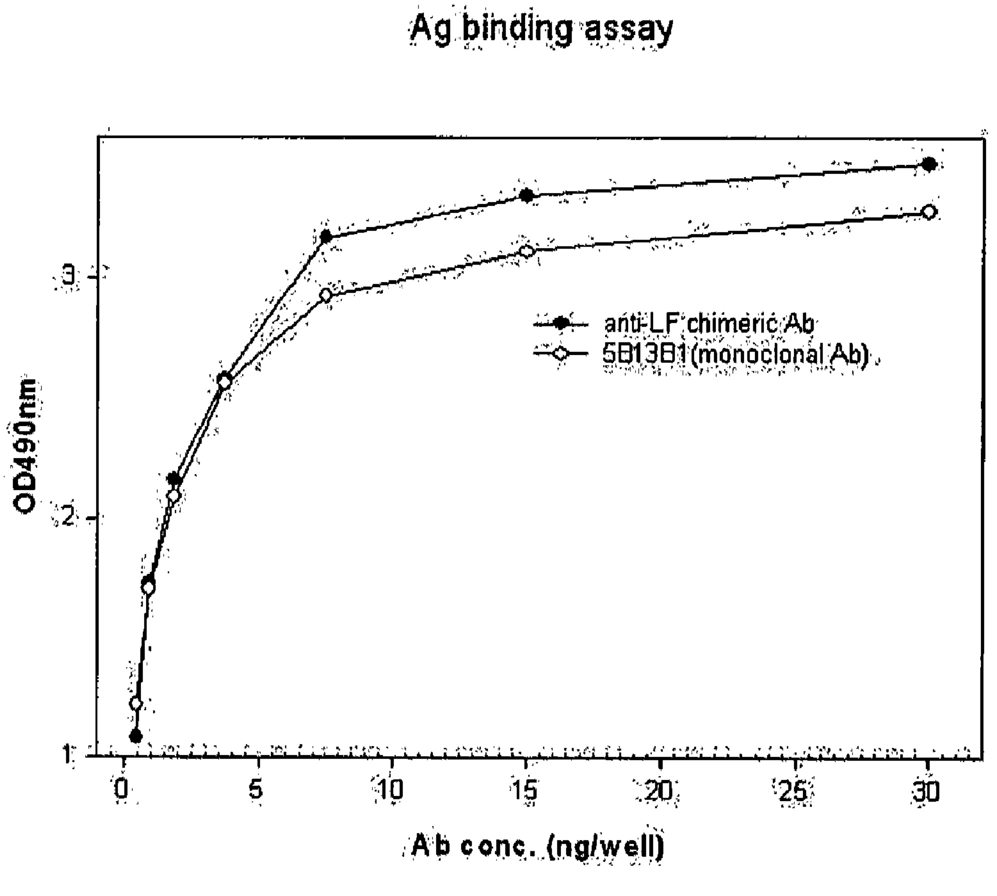
FIG. 15 shows the results of comparison of antigen binding ability of a chimeric antibody (anti-LF chimeric Ab) comprising the heavy chain and light chain of the 5B13B1 antibody with that of the 5B13B1 antibody.

Each well of a microplate was coated with 100 ng of the whole LF protein. The culture fluid of the COS7 cells transformed with the DNA-lipofectamine mixture was added to each well in concentrations of 0, 0.9, 1.8, 3.75, 7.5, 15 and 30 ng. Indirect ELISA was carried out using anti-human horseradish peroxidase-conjugated antibody as a secondary antibody, and absorbance was measured at 492 nm. As a control, anti-LF mouse antibody was used, and the same test was carried out. The results are given in FIG. 15. As shown in FIG. 15, the constructed chimeric recombinant antibody displayed antigen binding capacity similar to that of the murine monoclonal antibody produced by the hybridoma. These results indicate that recombinant antibodies constructed using the cloned gene of the antibody, which displayed precise binding capacity and neutralizing activity, have specificity and neutralizing activity identical to that of the parent antibody. Thus, various types of recombinant antibodies constructed using the gene of the present antibody may also be useful in the prevention, treatment and detection of anthrax.

EXAMPLE 7

Epitope Mapping

Figure 16:
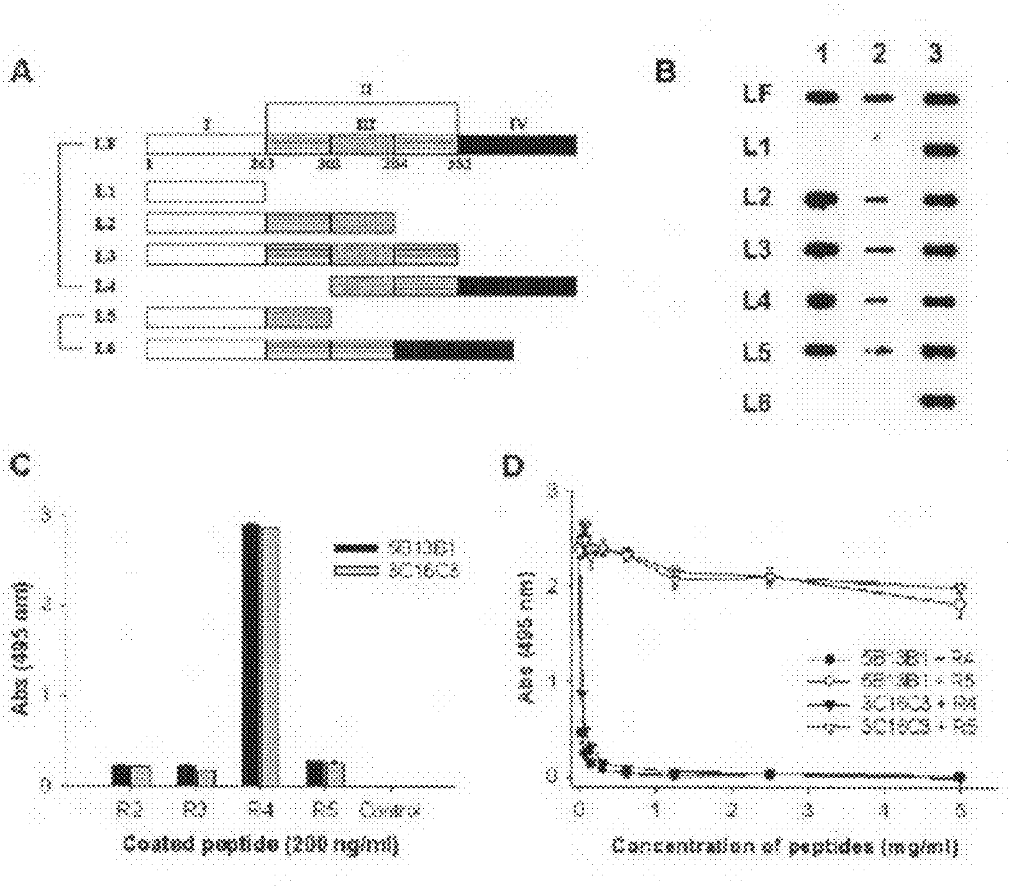
FIG. 16 shows the results of epitope mapping, (A) schematic representation of LF mutant constructs (L1 (domain I), L2 (domains I, partial II, and III), L3 (domains I, II, and III), L4 (domains partial II, III, and IV), L5 (domains I and III, and L6 (domains I, II, and IV)); (B) slot blot analysis of the six LF mutants and wild-type LF using 5B13B1 (lane 1), 3C16B6 (lane 2), and AP1 (lane 3) antibodies; (C) ELISA analysis of the four peptides corresponding to repeat sequences of the domain III of LF; and (D) competitive inhibition of 5B13B1 and 3C16C3 antibodies by peptides, wherein 5B13B1 and 3C16C3 antibodies competed with increasing concentrations of the peptides.

Deletion mutants of lethal factor (LF) were constructed through slot-blot analysis so as to identify a domain of an antigen, to which the present antibodies bind. To determine the epitope recognized by the LF-neutralizing antibodies, six deletion mutants (L1, L2, L3, L4, L5, and L6) of LF were constructed from pBS1-1 LF by PCR (FIG. 16, panel A). The L1, L2 and L3 mutants were synthesized using 1-3F as a 5' primer and 1R, 2R and 3R, respectively, as 3' primers. The L4 mutant was synthesized using 4F as a 5' primer and 4R as a 3' primer. To construct the L5 mutant, two PCR reactions were carried out using the 5' primer 1-3F and the 3' primer 5R, and the 5' primer 5F and the 3' primer 2R, and the two PCR products were subjected to recombinant PCR using the 5' primer 1-3F and the 3' primer 2R. To construct the L6 mutant, two PCR reactions were carried out using the 5' primer 1-3F and the 3' primer 6R, and the 5' primer 6F and the 3' primer 4R, and the two PCR products were subjected to recombinant PCR using the 5' primer 1 -3F and the 3' primer 4R. The final PCR products were digested with BamHI and XbaI and subcloned into the BamHI-XbaI sites of a pBS1-2 expression vector (Aprogen, Korea).

The resulting six deletion mutants of LF were expressed in *E. coli* HB2151 and purified by affinity chromatography using an Ap1-conjugated Sepharose column. After the size and other features of each purified protein were confirmed using Western blot analysis, the same amounts of the LF proteins were subjected to slot-blot analysis. 1 μg of the native LF or each of the mutant LF proteins was absorbed onto a nitrocellulose membrane. After being blocked with 2% BSA, the membrane was incubated with 5B13B1, 3C16B or Ap1 and then with HRP-conjugated goat anti-mouse IgG (Fc-specific) antibody. Protein bands were detected by chemiluminescence using an ECL kit (Intron, Korea).

The present antibodies were found to bind to mutants containing the domain III of LF, among the L1 to L4 mutants. Two additional mutants, L5 (domain I plus domain III) and L6 (full LF minus domain III), were constructed and subjected to slot blot analysis. The antibody reactivity was observed in L5, but not in L6. These results indicate that the epitope recognized by the present antibodies is on the domain III of LF (FIG. 16, panel B).

For fine epitope mapping, four peptides from the domain III were synthesized and conjugated to KLH. The sequences of the peptides were as follows.

(SEQ ID No. 37)

R2: Ac-HSLSQEEKELLKRIQIDC (SEQ ID No. 38)

R3: Ac-SDFLSTEEKEFLKKLQIDIC

-continued (SEQ ID No. 39)

R4: Ac-DSLSEEEKELLNRIQVDSC (SEQ ID No. 40)

R5: Ac-NPLSEKEKEFLKKLKLDIC

The binding of the monoclonal antibodies to each peptide was determined by indirect ELISA using 200 ng of the peptide-KLH conjugate as a coating antigen. A peptide (SEQ ID No. 41) derived from the F protein of respiratory syncytial virus (RSV) was used as a control. As a result, the present antibodies displayed very strong binding affinity to the amino acid sequence of the R4 peptide (FIG. 16, panel C). These results were consistent with the results of competitive inhibition, which are given in FIG. 16, panel D. For competitive inhibition, the antibodies were reacted with increasing concentrations of R4 and R5, and analyzed by ELISA using LF as a coating antigen. As a result, only R4 was found to competitively inhibit the binding of the antibodies to LF, indicating that the R4 repeat sequence is the epitope recognized by the present antibodies.

Industrial Applicability

The present antibodies specific to anthrax toxin have very high affinity and potent toxin-neutralizing activity, and effectively neutralize anthrax toxin when administered after as well as before exposure to anthrax toxin. Thus, the present antibodies are potentially useful as both preventive and therapeutic agents for anthrax.

The invention claimed is:

1. A monoclonal antibody, or an antigen binding fragment thereof, that specifically binds to domain III of *Bacillus anthracis* lethal factor, said antibody or antigen binding fragment comprising a heavy chain variable region (VH) and a light chain variable region (VL), said VH comprising the heavy chain complementarity determining regions (CDRs) comprising the amino acid sequences of SEQ ID NOs 3, 4, and 5, and said VL comprising the light chain CDRs comprising the amino acid sequences of SEQ ID NOs 8, 9, and 10.

2. The monoclonal antibody or antigen binding fragment of claim 1, wherein the domain III of *Bacillus anthracis* lethal factor comprises the amino acid sequence of SEQ ID NO. 42.

3. The monoclonal antibody or antigen binding fragment of claim 1, wherein said heavy chain variable region comprises the amino acid sequence of SEQ ID NO. 2, and said light chain variable region comprises the amino acid sequence of SEQ ID NO. 7.

4. The monoclonal antibody of claim 1, wherein the antibody is produced by a hybridoma having accession number KCTC 10756BP.

5. A hybridoma having accession number KCTC 10756BP.

6. An isolated nucleotide sequence encoding the heavy chain variable region of the antibody or antigen binding fragment of claim 1.

7. An isolated nucleotide sequence encoding the light chain variable region of the antibody or antigen binding fragment of claim 1.

8. A composition for neutralizing anthrax lethal factor comprising the antibody or antigen binding fragment of claim 1 and a pharmaceutically acceptable carrier.

9. The composition of claim 8, wherein the composition is formulated into a dosage form suitable for administration to a subject.

10. The composition of claim 9, wherein the dosage form is suitable for intravenous administration, subcutaneous administration, intracutaneous administration, oral administration, mucosal administration, intrathecal administration, or administration via inhalation.

11. A kit for detecting anthrax lethal factor comprising the antibody or antigen binding fragment of claim 1.

12. A method for treating intoxication by anthrax lethal factor in a subject comprising administering the antibody or antigen binding fragment of claim 1 to the subject in need thereof, thereby treating intoxication in the subject.

13. A composition for neutralizing anthrax lethal factor comprising the antibody or antigen binding fragment of claim 3 and a pharmaceutically acceptable carrier.

14. A composition for neutralizing anthrax lethal factor comprising the antibody or antigen binding fragment of claim 4 and a pharmaceutically acceptable carrier.

15. A kit for detecting anthrax lethal factor comprising the antibody or antigen binding fragment of claim 3.

16. A kit for detecting anthrax lethal factor comprising the antibody or antigen binding fragment of claim 4.

17. The monoclonal antibody or antigen binding fragment of claim 1, wherein said antibody or antigen binding fragment is a chimeric antibody or antigen binding fragment.

18. The monoclonal antibody or antigen binding fragment of claim 1, wherein said antibody or antigen binding fragment is a humanized antibody or antigen binding fragment.

19. The composition of claim 8, wherein the composition further comprises another therapeutic agent in order to enhance toxin neutralization.

20. The composition of claim 19, wherein the composition is a mixture.

21. The chimeric antibody or antigen binding fragment of claim 17, wherein the antibody or antigen binding fragment comprises a human gamma 1 ($\gamma 1$) heavy chain constant region, and a human kappa ($\kappa$) light chain constant region.

22. The humanized antibody or antigen binding fragment of claim 18, wherein the antibody or antigen binding fragment comprises a human heavy chain framework region derived from a human gamma 1 ($\gamma 1$), gamma 2 ($\gamma 2$), gamma 3 ($\gamma 3$), gamma 4 ($\gamma 4$), mu ($\mu$), alpha 1 ($\alpha 1$), alpha 2 ($\alpha 2$), delta ($\delta$), or epsilon ($\epsilon$) immunoglobulin heavy chain.

23. The humanized antibody or antigen binding fragment of claim 22, wherein the antibody or antigen binding fragment comprises a human heavy chain framework region derived from a human gamma 1 ($\gamma 1$) immunoglobulin heavy chain.

24. The humanized antibody or antigen binding fragment of claim 18, wherein the antibody or antigen binding fragment comprises a human light chain framework region derived from a human kappa ($\kappa$) or lambda ($\lambda$) immunoglobulin light chain.

25. The humanized antibody or antigen binding fragment of claim 24, wherein the antibody or antigen binding fragment comprises a human light chain framework region derived from a human kappa ($\kappa$) immunoglobulin light chain.

26. The antibody or antigen binding fragment of claim 1, wherein the antibody or antigen binding fragment specifically binds to amino acids 347-365 of domain III of *Bacillus anthracis* lethal factor, which comprises the amino acid sequence of SEQ ID NO. 39.

27. A method for inhibiting intoxication by anthrax lethal factor in a subject comprising administering the antibody or antigen binding fragment of claim 1 to the subject, thereby inhibiting intoxication in the subject.

28. A method for neutralizing anthrax lethal factor in a subject comprising administering the antibody or antigen binding fragment of claim 1 to the subject, thereby neutralizing anthrax lethal factor in the subject.

29. A method for enhancing toxin neutralization in a subject comprising administering the antibody or antigen binding fragment of claim 1 in combination with another therapeutic agent to the subject, thereby enhancing toxin neutralization in the subject.

30. A method for detecting lethal factor in a sample comprising contacting the sample with the antibody or antigen binding fragment of claim 1 and determining binding of a component of the sample to the antibody or antigen binding fragment, wherein the presence of binding is indicative of lethal factor in the sample.

* * * * *